(12) United States Patent
Scaboo et al.

(10) Patent No.: US 8,703,653 B2
(45) Date of Patent: Apr. 22, 2014

(54) QUANTITATIVE, HIGHLY MULTIPLEXED DETECTION OF NUCLEIC ACIDS

(75) Inventors: Kris Scaboo, Castro Valley, CA (US); Patrick Martin, San Carlos, CA (US); Brad Taft, San Francisco, CA (US); Jason La, San Francisco, CA (US)

(73) Assignee: NVS Technologies, Inc., Menlo Park, CA (US)

( * ) Notice: Subject to any disclaimer, the term of this patent is extended or adjusted under 35 U.S.C. 154(b) by 0 days.

(21) Appl. No.: 13/587,883

(22) Filed: Aug. 16, 2012

(65) Prior Publication Data
US 2013/0090252 A1    Apr. 11, 2013

Related U.S. Application Data

(63) Continuation-in-part of application No. 13/399,872, filed on Feb. 17, 2012, and a continuation-in-part of application No. PCT/US2012/025699, filed on Feb. 17, 2012.

(60) Provisional application No. 61/561,198, filed on Nov. 17, 2011, provisional application No. 61/463,580, filed on Feb. 18, 2011.

(51) Int. Cl.
*C12Q 1/68* (2006.01)
*C40B 30/04* (2006.01)
*G01N 21/64* (2006.01)

(52) U.S. Cl.
USPC .................................................. 506/9; 436/6

(58) Field of Classification Search
USPC ............................................................ 506/9
See application file for complete search history.

(56) References Cited

U.S. PATENT DOCUMENTS

| | | | |
|---|---|---|---|
| 6,270,965 B1 | 8/2001 | Kleiber et al. | |
| 6,350,580 B1 | 2/2002 | Sorge | |
| 7,170,555 B1 | 1/2007 | McCleary | |
| 7,189,508 B2 | 3/2007 | Sorge et al. | |
| 7,829,313 B2 | 11/2010 | Alexandre et al. | |
| 2002/0137197 A1 | 9/2002 | Ammann et al. | |
| 2004/0009514 A1 | 1/2004 | Frutos et al. | |
| 2005/0244821 A1 | 11/2005 | Zik et al. | |
| 2006/0281112 A1* | 12/2006 | Remacle et al. | 435/6 |
| 2007/0099211 A1 | 5/2007 | Aivazachvili et al. | |

(Continued)

FOREIGN PATENT DOCUMENTS

| | | |
|---|---|---|
| EP | 2 118 310 B1 | 3/2013 |
| WO | WO 2006/099255 A2 | 9/2006 |

(Continued)

OTHER PUBLICATIONS

Marras et al. Clinica Chimica Acta, 2006, 363, pp. 48-60.*

(Continued)

*Primary Examiner* — Larry Riggs
*Assistant Examiner* — Karla Dines
(74) *Attorney, Agent, or Firm* — Quine Intellectual Property Law Group, P.C.

(57) ABSTRACT

This invention provides methods of detecting and quantifying target nucleic acids in samples in multiplexed single chamber reactions. Consumables incorporating chambers optimized to reduce signal background proximal to high efficiency arrays are provided, as well as methods of use. Devices and systems configured to use the consumables to practice the methods are a feature of the invention.

18 Claims, 15 Drawing Sheets

(56) References Cited

U.S. PATENT DOCUMENTS

| | | |
|---|---|---|
| 2008/0193940 A1 | 8/2008 | Aivazachvili et al. |
| 2008/0241838 A1 | 10/2008 | Scaboo et al. |
| 2010/0047784 A1 | 2/2010 | Shlomit et al. |
| 2010/0248991 A1 | 9/2010 | Roesler et al. |
| 2010/0323355 A1 | 12/2010 | Dittmer |
| 2011/0039720 A1 | 2/2011 | Vossenaar et al. |

FOREIGN PATENT DOCUMENTS

| | | |
|---|---|---|
| WO | WO 2009/013220 A1 | 1/2009 |
| WO | WO 2010/058342 A1 | 5/2010 |
| WO | WO 2012/150749 A1 | 11/2012 |
| WO | WO 2012/150835 A2 | 11/2012 |

OTHER PUBLICATIONS

Juskowiak, Analytical Bioanalytical Chemistry, 2011, 399, 3, pp. 3157-3176.*

Shalon et al., Genome Research, 1996,6, pp. 639-645.*

Kapur et al., Genome Biology, 2007, 8, pp. R82 1-8.*

International Search Report and Written Opinion dated Jul. 18, 2013 from PCT/US2013/032691.

Aitichou et al. (2008) "Dual-probe real-time PCR assay for detection of variola or other orthopoxviruses with dried reagents," Journal of Virological Methods, 153(2):190-195.

Cissel (2010) "Luminescence-based microRNA detection methods," dissertation, Purdue University Graduate School, 142 pages.

Liu et al. (2006) "TaqMan probe array for quantitative detection of DNA targets," Nucleic Acids Research, 34(1):e4.

Pierik et al. (2012) "Real time quantitative amplification detection on a microarray: towards high multiplex quantitative PCR," Lab on a Chip, 12(10):1897-1902.

Wang et al. (2002) "Label-free hybridization detection of a single nucleotide mismatch by immobilization of molecular beacons on an agarose film," Nucleic Acids Research, 30(12):e61.

International Search Report and Written Opinion dated Dec. 26, 2012 from PCT/US2012/025699.

International Search Report and Written Opinion dated Jan. 31, 2013 from PCT/US2012/051236.

Matsubara et al. (2005) "Microchamber array based DNA quantification and specific sequence detection from a single copy via PCR in nanoliter volumes," Biosensors and Bioelectronics, 20(8):1482-1490.

Reck-Peterson et al. (2010) "Imaging single molecules using total internal reflection fluorescence microscopy (TIRFM)," Cold Spring Harbor Protocols, 2010(3):1-11.

Schrenzel et al. (2009) "Detection of highly dangerous pathogens: microarray methods for the detection of BSL3 and BSL4 agents," Wiley-VCH, Chapter 1, pp. 1-34.

* cited by examiner

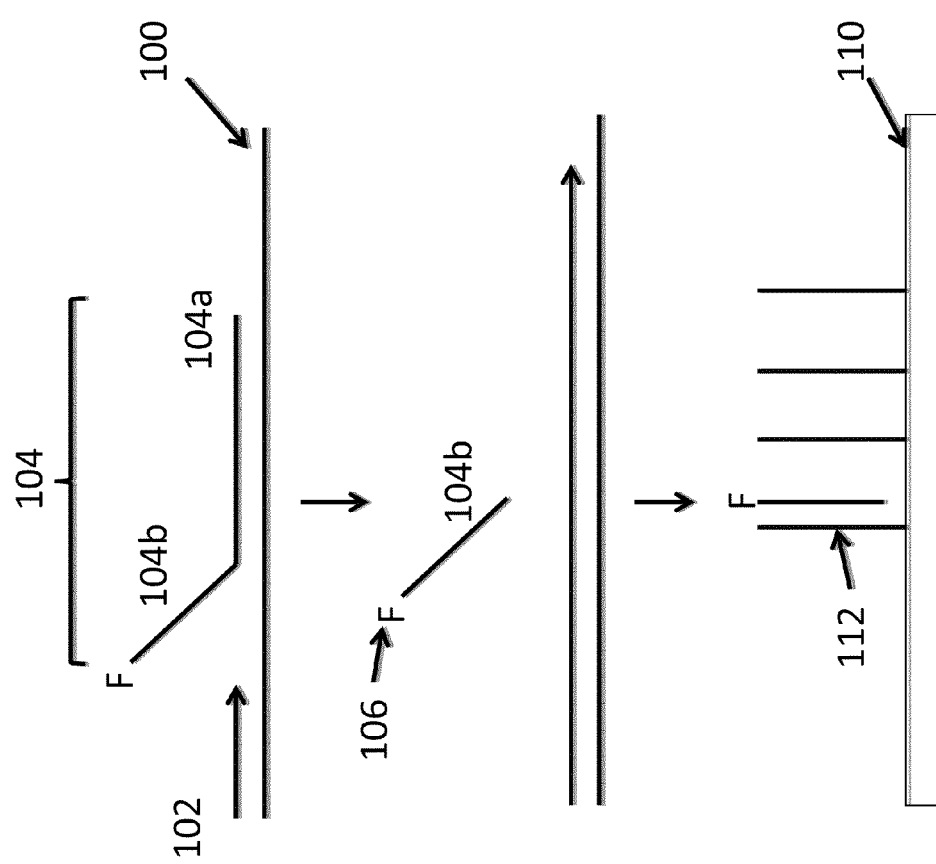

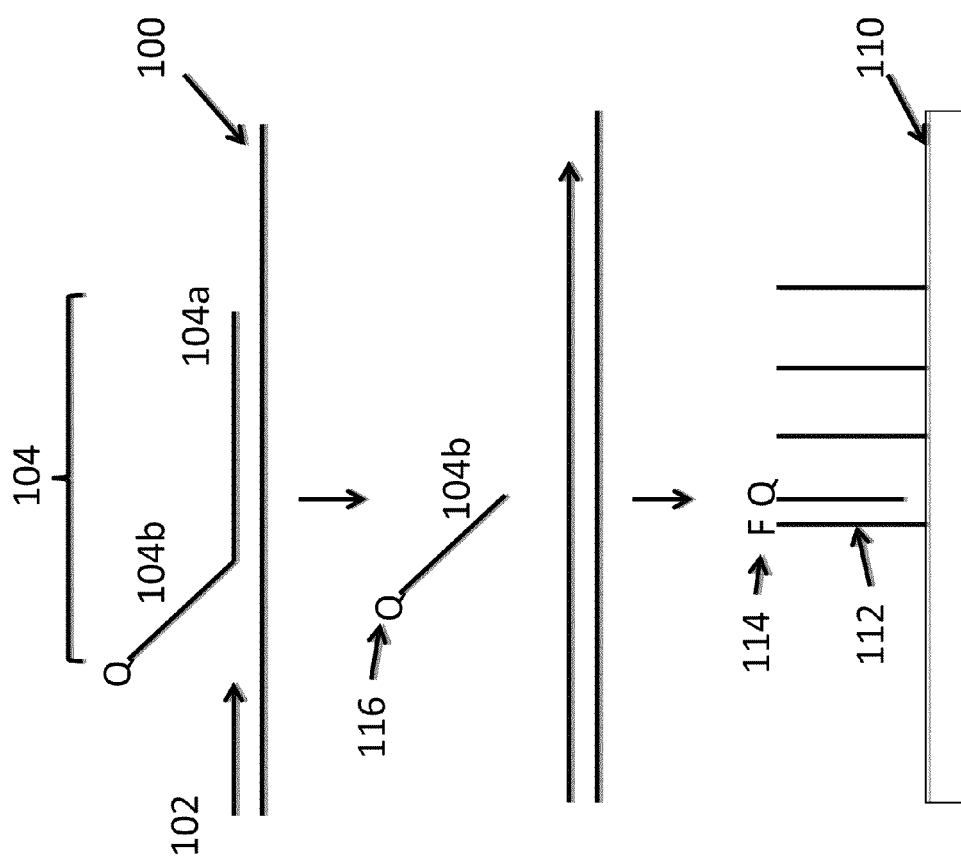

SEQUENCE LISTING

```
<160> NUMBER OF SEQ ID NOS: 20

<210> SEQ ID NO 1
<211> LENGTH: 57
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (46)..(54)
<223> OTHER INFORMATION: n is a, c, g, or t

<400> SEQUENCE: 1
nnnnnnnnnn nnncctgttg ccaatttcag agtgttttgc ttaacnnnnn nnnngat        57
```

```
<210> SEQ ID NO 2
<211> LENGTH: 56
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(27)
<223> OTHER INFORMATION: n is a, c, g, or t

<400> SEQUENCE: 2
nnnnnnnnnn nnnnnnnnnn nnnnnnatg gccgttagct tcagtcaatt caacag        56

<210> SEQ ID NO 3
<211> LENGTH: 45
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (38)..(45)
<223> OTHER INFORMATION: n is a, c, g, or t

<400> SEQUENCE: 3
nnnnnnnnnn nnntcgctga acaagcaacc gttacccnnn nnnnn                   45

<210> SEQ ID NO 4
<211> LENGTH: 54
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (47)..(54)
<223> OTHER INFORMATION: n is a, c, g, or t

<400> SEQUENCE: 4
nnnnnnnnnn nnncccatg gaatgttatc tcccttttaa gcttctnnnn nnnn          54

<210> SEQ ID NO 5
<211> LENGTH: 50
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (43)..(50)
<223> OTHER INFORMATION: n is a, c, g, or t

<400> SEQUENCE: 5
nnnnnnnnnn nnnaccttgg cgctattaga tttccatttg ccnnnnnnnn              50

<210> SEQ ID NO 6
<211> LENGTH: 58
<212> TYPE: DNA
<213> ORGANISM: Artificial Sequence
```

```
<220> FEATURE:
<223> OTHER INFORMATION: synthetic oligonucleotide probe
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (47)..(58)
<223> OTHER INFORMATION: n is a, c, g, or t

<400> SEQUENCE: 6
nnnnnnnnnn nnnncctgtt gccaatttca gagtgttttg cttaacnnnn nnnnnnnn          58

<210> SEQ ID NO 7
<211> LENGTH: 49
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (42)..(49)
<223> OTHER INFORMATION: n is a, c, g, or t

<400> SEQUENCE: 7
nnnnnnnnnn nnnntcaaag ccaattcgag cagctgaaac tnnnnnnnn                    49

<210> SEQ ID NO 8
<211> LENGTH: 49
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (38)..(49)
<223> OTHER INFORMATION: n is a, c, g, or t

<400> SEQUENCE: 8
nnnnnnnnnn nnntcgctga acaagcaacc gttacccnnn nnnnnnnnn                    49

<210> SEQ ID NO 9
<211> LENGTH: 54
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (47)..(54)
<223> OTHER INFORMATION: n is a, c, g, or t

<400> SEQUENCE: 9
nnnnnnnnnn nnncccatg gaatgttatc tcccttttaa gcttctnnnn nnnn               54

<210> SEQ ID NO 10
<211> LENGTH: 51
<212> TYPE: DNA
<213> ORGANISM: Artificial Sequence
```

```
<220> FEATURE:
<223> OTHER INFORMATION: synthetic oligonucleotide probe
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (44)..(51)
<223> OTHER INFORMATION: n is a, c, g, or t

<400> SEQUENCE: 10
nnnnnnnnnn nnnnaccttg gcgctattag atttccattt gccnnnnnnn n          51

<210> SEQ ID NO 11
<211> LENGTH: 56
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (46)..(56)
<223> OTHER INFORMATION: n is a, c, g, or t

<400> SEQUENCE: 11
nnnnnnnnnn nnncctgttg ccaatttcag agtgttttgc ttaacnnnnn nnnnnn      56

<210> SEQ ID NO 12
<211> LENGTH: 48
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (41)..(48)
<223> OTHER INFORMATION: n is a, c, g, or t

<400> SEQUENCE: 12
nnnnnnnnnn nnntcaaagc caattcgagc agctgaaact nnnnnnnn              48

<210> SEQ ID NO 13
<211> LENGTH: 45
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (38)..(45)
<223> OTHER INFORMATION: n is a, c, g, or t

<400> SEQUENCE: 13
nnnnnnnnnn nnntcgctga acaagcaacc gttacccnnn nnnnn                 45

<210> SEQ ID NO 14
<211> LENGTH: 50
<212> TYPE: DNA
<213> ORGANISM: Artificial Sequence
```

```
<220> FEATURE:
<223> OTHER INFORMATION: synthetic oligonucleotide probe
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (44)..(50)
<223> OTHER INFORMATION: n is a, c, g, or t

<400> SEQUENCE: 14
nnnnnnnnnn nnnnatggcc gttagcttca gtcaattcaa cagnnnnnnn                50

<210> SEQ ID NO 15
<211> LENGTH: 53
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (45)..(53)
<223> OTHER INFORMATION: n is a, c, g, or t

<400> SEQUENCE: 15
nnnnnnnnnn nnnttggaat tgtctcgaca acaatctttg gcctnnnnnn nnn            53

<210> SEQ ID NO 16
<211> LENGTH: 55
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (48)..(55)
<223> OTHER INFORMATION: n is a, c, g, or t

<400> SEQUENCE: 16
nnnnnnnnnn nnnccattta cctaagtgat ggaatcaatc gcaaaagnnn nnnnn          55

<210> SEQ ID NO 17
<211> LENGTH: 54
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (46)..(54)
<223> OTHER INFORMATION: n is a, c, g, or t

<400> SEQUENCE: 17
nnnnnnnnnn nnnnnacata agctttgatc aaccctatgc tgcacnnnnn nnnn           54

<210> SEQ ID NO 18
<211> LENGTH: 50
<212> TYPE: DNA
<213> ORGANISM: Artificial Sequence
```

-continued

```
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (42)..(50)
<223> OTHER INFORMATION: n is a, c, g, or t

<400> SEQUENCE: 18
nnnnnnnnnn nnnttcgaag gctccacata cacagctgct gnnnnnnnnn         50

<210> SEQ ID NO 19
<211> LENGTH: 48
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (41)..(48)
<223> OTHER INFORMATION: n is a, c, g, or t

<400> SEQUENCE: 19
nnnnnnnnnn nnntcgaagg ctccacatac acagctgctg nnnnnnnn           48

<210> SEQ ID NO 20
<211> LENGTH: 51
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (44)..(51)
<223> OTHER INFORMATION: n is a, c, g, or t

<400> SEQUENCE: 20
nnnnnnnnnn nnnttcggca tttcctggat tgagtcggta ctannnnnnn n        51
```

QUANTITATIVE, HIGHLY MULTIPLEXED DETECTION OF NUCLEIC ACIDS

CROSS-REFERENCE TO RELATED APPLICATIONS

This application is a continuation-in part of U.S. patent application No. 13/399,872, filed Feb. 17, 2012, and International Application No. PCT/US 2012/025699, filed Feb. 17, 2012, both of which claim priority to Provisional U.S. Patent Application No. 61/463,580, filed Feb. 18, 2011, and Provisional U.S. Patent Application No. 61/561,198, filed Nov. 17, 2011, the full disclosures of each of which are hereby incorporated herein by reference in their entirety for all purposes.

This application claims priority as a continuation in part to U.S. patent application Ser. No. 13/399,872, filed Feb. 17, 2012, which claims priority to Provisional U.S. Patent Application No. 61/463,580, filed Feb. 18, 2011, and Provisional U.S. Patent Application No. 61/561,198, filed Nov. 17, 2011, the full disclosures of each of which are hereby incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with support of a U.S. Dept. of Homeland Security grant, Contract Number HSHQDC-10-C-00053. The government may have certain rights in the invention.

FIELD OF THE INVENTION

The invention is in the field of real-time DNA amplification, detection and quantification, as well as associated consumables, devices, and systems, including arrays.

BACKGROUND OF THE INVENTION

Real time PCR is routinely used for detection of nucleic acids of interest in a biological sample. For a review of real time PCR see, e.g., M Tevfik Dorak (Editor) (2006) *Real-time PCR (Advanced Methods)* Taylor & Francis, 1st edition ISBN-10: 041537734X ISBN-13: 978-0415377348, and Logan et al. (eds.) (2009) *Real-Time PCR: Current Technology and Applications*, Caister Academic Press, 1st edition ISBN-10: 1904455395, ISBN-13: 978-1904455394. For additional details, see also, e.g., Gelfand et al. "Homogeneous Assay System Using The Nuclease Activity of A Nucleic Acid Polymerase" U.S. Pat. No. 5,210,015; Leone et al. (1995) "Molecular beacon probes combined with amplification by NASBA enable homogenous real-time detection of RNA." *Nucleic Acids Res.* 26:2150-2155; and Tyagi and Kramer (1996) "Molecular beacons: probes that fluoresce upon hybridization" *Nature Biotechnology* 14:303-308. Traditionally, single well multiplexing, used to detect more than one target nucleic acid per sample in a single reaction container (e.g., well of a multiwell plate), is achieved using self-quenched PCR probes such as TAQMAN™ or Molecular Beacon probes that are specific for each amplicon. Upon binding to the amplicon in solution, or upon degradation of the probes during PCR, the probes unquench, producing a detectable signal. The probes are labeled with fluorophores of different wavelengths, permitting a multiplexing capability of up to about 5 targets in a single "one pot" reaction. More than about 5 probes per reaction is difficult to achieve, due to practical spectral range and label emission limitations. This severely limits multiplexing of a single reaction, which, in turn, significantly limits how many targets can be screened per sample and drives up reagent cost and instrument complexity in detecting multiple targets of interest.

Nucleic acid arrays represent another approach to multiplexing the detection of amplification products. Most typically, amplification reactions are performed on a sample, and amplicons are separately detected on a nucleic acid array. For example, Sorge "Methods for Detection of a Target Nucleic Acid Using A Probe Comprising Secondary Structure" U.S. Pat. No. 6,350,580 propose the capture of a probe that is released upon amplification by purifying the probe out of the amplification mixture and then detecting it. This multiple-step approach to making and detecting amplicons makes real time analysis of the amplification mixture impractical.

Various approaches that amplify the reactants in the presence of the capture nucleic acids have also been proposed. For example, Kleiber et al. "Integrated Method and System for Amplifying And Detecting Nucleic Acids," U.S. Pat. No. 6,270,965, propose detection of an amplicon via evanescence induced fluorescence. Similarly, Alexandre et al "Identification and Quantification of a Plurality of Biological (Micro) Organisms or Their Components," U.S. Pat. No. 7,829,313, proposes detection of amplicons on arrays. In another example, target polynucleotides are detected by detecting a probe fragment that is produced as a result of amplification, e.g., by binding to an electrode, followed by electrochemical detection. See, e.g., Aivazachvilli et al. "Detection of Nucleic Acid Amplification" US 2007/0099211; Aivazachvilli et al. "Systems and Methods for Detecting Nucleic Acids" US 2008/0193940, and Scaboo et al. "Methods And Systems for Detecting Nucleic Acids" US 2008/0241838.

These methods all suffer from practical limitations that limit their use for multiplex target nucleic acid detection. For example, Kleiber (U.S. Pat. No. 6,270,965) relies on evanescence induced fluorescence to detect fluorescence of amplicons at the array surface, and requires complex and expensive optics and arrays. Alexandre (U.S. Pat. No. 7,829,313) propose detection of amplicons on an array; as in Kleiber this increases array costs significantly, because each array has to be custom designed to detect each amplicon. In practice, it can be difficult to achieve similar hybridization kinetics for disparate amplicons on an array, particularly where the amplicons are relatively large, as in Alexandre. Furthermore, this art provides little guidance regarding how to detect signal on an array where there is an accompanying solution phase that also comprises high levels of signal background, or of arrays that remain stable through in situ thermal cycling.

The present invention overcomes these and other problems in the art. A more complete understanding of the invention will be obtained upon complete review of the following.

SUMMARY OF THE INVENTION

The invention provides methods and associated devices, systems and consumables that permit highly multiplexed detection of nucleic acids of interest, e.g., for the detection of viruses, bacteria, plasmodium, fungi, or other pathogens in a biological sample. The consumable comprises a signal-optimized chamber having a high-efficiency thermo-stable nucleic acid detection array on an interior surface of the chamber. The array is configured to detect up to about 100 or more different universal labeled probes. The methods generate the labeled universal probes (as "probe fragments") during amplification of a portion of a nucleic acid of interest, with the amplification reaction being performed in the chamber. The universal probes are hybridized to the array after a few amplification cycles, and subsequent to selected amplification cycles thereafter, allowing for both detection and quantification of one or more nucleic acids of interest in the sample, in real time.

Accordingly, in a first aspect, methods of detecting a target nucleic acid are provided. This includes providing a detection chamber that has at least one high efficiency nucleic acid detection array on at least one surface of the chamber. The high efficiency array typically has a non-rate limiting number of capture nucleic acids that permits an increased capture rate of detectable probe fragments produced by a reaction in the chamber, and the capture nucleic acids are configured to capture relatively small probe nucleic acids, which also increases array efficiency. Detection of binding of the probes to the array is preferably carried out under conditions that are selected or configured to reduce background signal levels proximal to the array, e.g., resulting from unbound free probe. For example, in certain embodiments, the chamber itself is configured to reduce signal background proximal to the array, e.g., by shaping the chamber to reduce background (e.g., by making the chamber relatively thin proximal to the array, e.g., the chamber is typically about 500 μm or shallower above the array). Thinner chambers also have less thermal mass, and can be temperature cycled more rapidly and more efficiently than thicker chambers. Other ways in which the system and methods are configured to reduce the level of background signal are described in greater detail, below.

A sample that has one or more copies of the target nucleic acid to be detected is loaded into the detection chamber. An amplification primer and a labeled probe are hybridized to the one or more target nucleic acid copies. At least a portion of one or more of the target nucleic acid copies is amplified in an amplification primer dependent amplification reaction. The amplification reaction results in cleavage of the labeled probe, e.g., due to nuclease activity of an amplification enzyme. This results in release of a labeled probe fragment, which is to be detected by the array. The labeled probe fragment is hybridized to the high-efficiency array (typically after a few amplification cycles are run to amplify the amount of probe fragment released in the chamber). A label signal produced by binding the labeled probe fragment to the array is then detected, thereby detecting the target nucleic acid.

The precise configuration of the detection chamber can vary. The configuration is selected to reduce signal background in the chamber proximal to the array. Generally, at least 1%, and often, about 5% or more of the signal in the chamber is concentrated at the array (e.g., about 6%, 8%, or even 10% or more) in the region of the array. Background of 99% or less total signal can be normalized by the system, though lower levels are often desirable. In typical embodiments described herein, levels of 95% or less total background are achieved by optimizing the configuration of the chamber proximal to the array. This configuration optimization is achieved, e.g., by keeping the depth of the chamber above the array to a minimum. In typical embodiments, the chamber is less than about 1 mm in depth or other dimension proximal to the array, more typically about 500 μm or less in at least one dimension proximal to the array, preferably less than about 250 μm or less, e.g., between about 10 μm and about 200 μm and in some embodiments the chamber is about 150 μm in a dimension proximal to the array. In one example herein, the chamber is about 142 μm in depth above the array. In another example herein, the chamber is about 100 μm in depth. The relevant chamber dimension depends on the signal detection path of the detection system, for example, where the signal is generated by passing light onto the array, where some of the light escapes through the array and into the fluid above the array, the relevant dimension is the depth of the chamber above the array. In addition to reducing the level of background signal detected, reducing chamber thickness also has the benefit of reducing the contribution of background noise components, e.g., detector responses unrelated to the specific detection of array spot signal and background signal from the reaction fluid. In particular, one major noise contributor is the shot noise from the detectors used, which generally increases with the square root of the total amount of signal detected, which, in turn, scales with the thickness of the reaction chamber. Accordingly, by providing reduced thickness of the reaction chamber, one reduces the background noise, and consequently increases the signal to background noise ratio (SNR) of the overall system. Other potential noise contributors include detection of excess light, e.g., unfiltered excitation light, unintended ambient light, scattered fluorescence, autofluorescence of system components, or the like. A number of these noise contributors may be mitigated through the conventional approaches, such as through the use of appropriate optical filters, e.g., to eliminate or reduce excess excitation light, sealed optical systems that reduce or prevent ambient light at the detector, and through the configuration of array spot size and spacing to reduce or eliminate signal cross talk at the detector. In particularly preferred aspects, the SNR for the assay methods and systems of the invention will typically be 2.5 or greater, preferably greater than 3, greater than 4, greater than 5, greater than 10, and in some cases, greater than 20 or more.

Alternative or additional approaches for configuring the system and methods of the invention to reduce background signal can also be employed in conjunction with the devices and methods of the invention. For example, the devices and systems of the invention may be configured to provide excitation illumination to the capture array using a total internal reflection fluorescence microscopy ("TIRF") configuration, where excitation light is directed into the substrate underlying the capture array such that it is entirely internally reflected (see, M. Tokunaga et al., Biochem. and Biophys. Res. Comm. 235, 47 (1997) and P. Ambrose, Cytometry, 36, 244 (1999)). Notwithstanding this, an evanescent wave is generated at the substrate-fluid interface of the array that decays exponentially away from the surface, resulting in effective illumination adjacent to the surface, e.g., to a depth of 100 nm, without exciting fluorophores in the remainder of the solution.

In still another alternative or additional approach, the reactants employed in the analytical methods of the invention are configured to reduce background signal relative to actual probe/array binding signal. For example, background signal may be reduced through the use of cooperative fluorophores on both the capture array probes and the labeled probe fragment, e.g., in a FRET construct. In particular, a donor fluorophore, having a first excitation spectrum and a first emission spectrum may be coupled to one of the capture probe or the labeled probe fragment. An acceptor fluorophore that has an excitation spectrum that overlaps the emission spectrum of the donor, and that is different from the donor's excitation spectrum, is coupled to the other probe. When the capture probe and labeled probe fragment hybridize, the donor and acceptor are brought into sufficient proximity for energy transfer, yielding a distinctive fluorescent signal corresponding to the emission spectrum of the acceptor fluorophore. By configuring the optical system to excite only within the donor's excitation spectrum, and filter the emission spectrum of the donor, one can selectively detect signal arising from the energy transfer signal from the acceptor, upon hybridization.

A wide variety of FRET label pairs have been described previously (See, e.g., U.S. Pat. Nos. 6,008,373, to Waggoner, and 7,449,298, to Lee et al.).

In an alternative configuration, interactive labeling groups are employed to further reduce the potential for background signals. In particular, in an aspect of the invention, the capture probe is labeled with a fluorophore such that the signal producing label is tethered to the surface of the array. In this context, the labeled probe and labeled probe fragment carries a quencher group complementary to the fluorophore, i.e., able to quench the fluorescence of the capture probe label. The quencher is provided on a position of the labeled probe fragment such that when hybridized to the capture probe, it will be sufficiently proximal to the fluorophore on the capture probe to quench the fluorescent signal. For example, where the labeled probe fragment is labeled with a quencher at its 5' end, the capture probe will bear the fluorophore at a 3' or other complementary position. In the context of the assays of the invention, amplification of the target sequence results in production of labeled probe fragments that quench the fluorescent signals from the array when it hybridizes with the labeled capture probe, resulting in a negative signal event as indicative of the presence of target signal. In particular, the capture probes on the array produce signal in the unhybridized state. Upon amplification of the target sequence, the quencher bearing probe fragment is released to hybridize to the complementary capture probe on the array, quenching the signal from its associated fluorophore, and resulting in a dark location on the array, as compared to unhybiridized array locations. By providing a quencher group that does not produce a fluorescent signal under detection conditions for the assay, any background fluorescence from the uncleaved probe or unbound labeled probe fragment is eliminated.

As will be appreciated, a number of methods may be employed in the context of the invention for reducing the contribution of signal from unbound, intact labeled probe in the reaction solution, or background signal, relative to the signal detected from bound labeled probe fragment, including, for example, configuring the reaction chamber to concentrate signal within the focal plane of the detector, employing interactive labeling techniques that either present different emission spectra when bound to the array versus when unbound in solution, or self quenching probes that have reduced fluorescence when present in the same intact probe, versus when separated in a cleaved probe fragment.

As noted, the array typically includes a non-rate limiting number of capture nucleic acids that hybridize to the labeled probe fragment. This means that the amplification reaction produces a number of probe fragments during amplification that results in a probe fragment concentration in the reaction mixture that is not saturating for the number of sites on the array (e.g., accessible complimentary capture nucleic acids) available to bind the probe fragments. Restated, the number of binding sites on the array is maintained in excess, and preferably well in excess, of what would be saturated at the concentration of probe fragments produced in an amplification reaction. Because the number of sites on the array is not rate limiting, the ratio of probe fragments on the array to background probe fragments in solution is optimized. Typical array densities are between about 350 fmol/cm$^2$ or greater, e.g., about 2,000 fmol/cm$^2$ or greater, 2,500 fmol/cm$^2$ or greater, 3,000 fmol/cm$^2$ or greater, 4,000 fmol/cm$^2$ or greater, 4,500 fmol/cm$^2$ or greater, or 5,000 fmol/cm$^2$ or greater. In some embodiments, the number of sites that bind probe on the array is at least 1× the number of sites that would be saturated by the concentration of probe fragments produced during amplification, and is optionally 5×, 10×, 50× or more. The ratio will vary with the number of amplification cycles and the amount of probe produced. The efficiency of the array is also a function of the length of the probe fragment to be captured. Shorter fragments typically display more efficient hybridization, although the probes do have to be long enough to bind at a given $T_m$ during hybridization. Typical probe fragments to be captured by the array are about 50 nucleotides in length or less; the arrays comprise sites that have corresponding complimentary capture nucleic acid sequences (the capture nucleic acids can optionally also include additional sequences, e.g., to space the complimentary site above the surface, e.g., to reduce surface effects). More typically, the probes and capture sequences are about 40 nucleotides or less in length, e.g., about 30, about 20, or about 15 nucleotides or shorter in length.

In some cases, the capture array probes, and complementary labeled probe fragments used in a given analysis are selected such that they provide a narrow range of Tm over all members of the array. In particular, to ensure optimal and consistent hybridization to the capture array, the capture probes in a given array will each have a Tm within about 10° C. of every other member of the array, and preferably, within about 7° C., 5° C., or 3° C. of every other probe in the array. Such a narrow $T_m$ range allows for consistent hybridization and resulting signal generation across all members of the array.

In typical embodiments, the hybridization temperature is less than the temperature of the amplification reaction, so the $T_m$ of the probe fragment for the capture nucleic acid can be less than an intra-molecular $T_m$ of the probe (e.g., where the probe comprises a quencher to reduce background), and/or lower than the $T_m$ of the probe for the target nucleic acid. That is, in typical thermocycling embodiments, amplification reactions are performed at higher temperatures than hybridization steps; accordingly, the probe will typically have a higher $T_m$ for the target nucleic acid than the probe fragment has for the array. The labeled probe typically comprises a first orthogonal flap that is not complimentary to the target nucleic acid; this flap is cleaved from the labeled probe to produce the labeled probe fragment. The labeled probe optionally comprises a second orthogonal flap, e.g., coupled to a quencher moiety, which is at least partially complimentary to the first flap (e.g., to provide proximity-based quenching of a label on the first flap). Background is reduced where the second flap has a higher $T_m$ for binding to the first flap than the first flap has for binding to the array. In such a configuration, the extension reaction occurs at a first temperature, i.e., below the $T_m$ of the intact probe for the target nucleic acid, but above both the intra-molecular $T_m$ of the intact probe, and the $T_m$ of the probe fragment for the capture probe on the array). Following extension, as the reaction temperature is lowered, it crosses below the intra-molecular $T_m$ of the probe, allowing for the formation of the secondary structure of the probe, and resultant quenching of the fluorophore. Further cooling to below the $T_m$ of the probe fragment to the capture probe allows hybridization of the probe fragment to the array and detection of its associated fluorophore. Because the intact probe has previously formed into its secondary structure, it is both less likely to bind to the capture probe, and is quenched, thus reducing both unintended capture of intact probe, and background signal from the fluorophores present on the intact probe in solution (or that may have bound to the capture probe array. Although in certain aspects, quenchers are employed on the intact probes of the invention, in certain embodiments it has been surprisingly determined that, quenchers are not required on the probe, because the optimized chamber design and high efficiency array achieve discrimination of array signal from background, even where background is increased by omitting a quencher from the probe.

In other embodiments, the labeled probe fragment and its complementary capture nucleic acid is designed or selected to have a $T_m$ that is higher than the extension reaction temperature, e.g., 10 or more degrees higher. Thus, where the extension reaction is carried out, for example, at between 55° and 60° C., the $T_m$ of the labeled probe fragment and capture nucleic acid will typically be, e.g., 71° C. In such cases, hybridization of the labeled probe fragment to the capture nucleic acid on the array occurs at the same temperature as the extension reaction, obviating the need to further reduce the temperature in order to hybridize to the array and detect the resulting signal. As a result, a two-step temperature profile may be used rather than a three step profile.

In the context of the intact labeled probe, the orientation of the orthogonal labeled probe fragment relative to the probe portion that binds to the target sequence, may be varied. In particular, a release labeled probe fragment may hybridize to a capture probe on the array in an orientation where the end cleaved from the target specific portion of the probe is either proximal or distal to the point at which the capture probe is coupled to the array surface. In some cases, for example, by ensuring that any intact probe would only bind to the capture probe in an orientation that projected the target specific portion of the probe toward the surface of the array, one could then take advantage of potential surface interference with that binding, to further reduce the potential for undesired capture of intact probe by the array. Such methods are particularly useful in the case of solid surfaces on the arrays, e.g., silica substrates and the like.

Sample can be loaded into the chamber by any of a variety of mechanisms, depending on the precise configuration of the consumable. In one convenient application, the sample is loaded through at least one port or fluidic channel in operable communication with the chamber. For example, ports can be fabricated in a top surface of the consumable, with the ports leading into the chamber. This provides for simplified loading, e.g., via a pipette or other fluid delivery device. Alternatively, fluidic or microfluidic channels, capillaries, or the like, can be used for sample delivery.

The methods can be used for detection of a nucleic acid of interest in a sample and/or quantification of the nucleic acid, e.g., in real time. Thus, in one aspect, the target nucleic acid is optionally amplified in a plurality of amplification cycles prior to detecting signal, with the target nucleic acid portion additionally being amplified after signal detection, i.e., in the presence of additional copies of the labeled probe. Resulting released labeled probe fragments are subsequently hybridized to the array and detected, with detected signal intensity being correlated to presence and/or quantity of the target nucleic acid present in the sample. Typically, the sample is amplified for more than 1 cycle before initial detection, to increase the level of signal by increasing the number of probe fragments released by the amplification. For example, the target nucleic acid can optionally be amplified for at least, e.g., 2, 3, 4, 5 or more amplification cycles prior to detecting signal from the array.

The labeled probe typically comprises a fluorescent or luminescent label, although other labels such as quantum dots can also be used. In one preferred embodiment, the label is a fluorescent dye. The signal produced by the probe fragment is typically an optical signal. The labeled probe optionally comprises a label and a label quencher; cleavage of the labeled probe results in separation of the label and the quencher, thereby unquenching the label. However, as noted above, quenchers are not required in the practice of the invention.

Signal is typically detected by detecting one or more optical signal wavelengths corresponding to optical labels on the probes or probe fragments. Because binding position of probe fragments on the array can be used to discriminate between different probes, it is not necessary to use different labels on the different probes to distinguish the probes in a multiplexed amplification reaction (an amplification reaction designed to amplify multiple target nucleic acids, if more than one of the targets is present in the sample). However, multiple probes labels can be used to enhance multiplexing capabilities. Where multiple probes are used, detecting the signal can include detecting a plurality of optical signal wavelengths from a plurality of signals generated by a plurality of different labels (e.g., different fluorescent dye moieties on different probes).

Although generally described in terms of label groups that are attached to the probe fragment that binds to the array, e.g., the labeled probe fragment, it will be appreciated that other detection schemes may be employed that do not require the use of pre-labeled probes. For example, in some embodiments, intercalating dyes may be used. Intercalating dyes typically provide a detectable signal event upon incorporation, or intercalation, into double stranded nucleic acids. In the context of the invention, the hybridization of the cleaved probe fragment to the complementary probe on the array creates a double stranded duplex at the array surface which could incorporate an intercalating dye, and provide a unique signal indiciative of that hybridization. Intercalating dyes are well known in the art and include those described in, e.g., Gudnason et al., Nucleic Acids Research, (2007) Vol. 35, No. 19, e127, which is incorporated herein by reference for all purposes. Similarly, although optical signal detection methods are particularly preferred, the probe configurations and assay methods may also generally be practiced using non-optical labeling and/or detection methods, e.g., using electro-chemical detection methods, e.g., ChemFETS, ISFETS, etc., optionally in conjunction which electrochemical labeling groups, e.g., possessing large charged groups to amplify detection of hybridization of the probe fragment to an array probe at or near a detector surface.

Local background can be detected for one or more regions of the array, with signal intensity measurements being normalized by correcting for said background. Typically, the normalized signal intensity is less than about 10% of total signal, e.g., between about 1 and about 10% of the total signal. In one example class of embodiments, the normalized signal intensity is between about 4 and about 7% of total signal. Typically, where approximately 1% or more of the signal is localized to the array, e.g., where about 1%, 2%, 3%, 4%, 5%, 6%, 7%, 8%, 9%, 10% or more of the signal is localized to the array for a region of the chamber, it is possible to discriminate the array signal from background. It is possible to discriminate even lower levels of signal to background, but this is not generally preferred. The methods can also include normalizing signal intensity by correcting for variability in array capture nucleic acid spotting (e.g., by correcting for spot size, spot density, or both), or by correcting for uneven field of view of different regions of the array.

The ability to simultaneously detect multiple target nucleic acids in a sample represents a preferred aspect of the invention. The sample may have one or a plurality of target nucleic acids, with the array comprising a plurality of capture nucleic acid types that are capable of detecting more than one target per sample. The capture nucleic acid types are spatially separated on the array, eliminating the need for the use of multiple labels (although, as noted, multiple labels can be used). In multiplex approaches, a plurality of amplification probes, each specific for a different nucleic acid target, is incubated with the sample, which can include one or more target nucleic acids. For example, there can be between about 5 and about 100 or more capture nucleic acid types. Each potential target to be detected will utilize a different probe as well, e.g., there are optionally between about 5 and about 100 or more labeled probe types in the amplification reaction, each specific for a potential target of interest. The array includes corresponding capture nucleic acids, e.g., between about 5 and about 100 or more capture nucleic acid types. This permits a corresponding number of signals to be detected and processed by the array. For example, between about 5 and about 100 or more different signals can be detected based upon positioning of the signals on the array after hybridization of the probe fragments to the array. As will be appreciated, the number of capture probe types on an array will generally be dictated by the number of distinct amplification reactions that can be multiplexed within a single reaction volume. However, capture arrays having larger numbers of different capture probes, e.g., greater than 100, greater than 1000, 10,000 or more capture probe types, may also be employed in some circumstances, e.g., where amplification reactions are pooled for interrogation by the array, or the like.

An advantage of the present invention is that one capture array configuration may be used for multiple different target nucleic acid sequence panels. In particular, a probe set for a first panel will include probes that have first target specific portions specific for the targets in the panel, and second capture portions complementary to individual probes on the capture array. A probe set for a second different panel (whether partially overlapping, or completely different) will include target specific portions for that panel, while the capture portions will be the same as for the first panel's probe set. Restated, for any panel of targets, the probe set will include a semi-fixed portion of the probes used for that panel, which will always be complementary to a member of the capture array. The probes will also include variable portions that are selected for the specific panel of target nucleic acids. For example, in an analytical process, a first set of probes is employed where each probe in the first set has a first fixed portion that corresponds to a different capture probe on the capture probe array. Each probe also includes a target specific portion that is complementary to a given target sequence in the first panel. For a second panel, a second set of probes is employed where each probe in the set includes the same first fixed portion, but has a second target specific portion that is specific for the targets in that panel.

With reference to FIG. 1A, portion A of the labeled probe corresponds to the variable portion, while portion B would correspond to the fixed portion that would be complementary to the probes on the array. The use of a universal or common capture array and capture probe set allows for more efficient and lower cost manufacturing of the consumables used in the invention.

Thus, in one embodiment in which the sample comprises multiple target nucleic acids, the method includes incubating a plurality of labeled probes, each specific for a different target nucleic acid, with the target nucleic acids. Amplifying at least a portion of the target nucleic acids in the amplification primer dependent amplification reaction results in cleavage of a plurality of labeled probe types and resulting release of a plurality of labeled probe fragment types. The plurality of probe fragment types are hybridized to the array. Each of the different probe fragment types hybridizes to a spatially discrete capture nucleic acid type. Detecting the label signal includes detecting a plurality of label signals from a plurality of spatially discrete regions corresponding to the spatially discrete capture nucleic acids on the array. Optionally, and in several preferred embodiments, the labeled probe types comprise the same label moiety, but additional multiplexing and/or use of differentially controls or registration probes can include using a plurality of different label moieties. Typically, the labeled probe types can include one or more different label moieties, with the number of different moieties being less than the number of labeled probe types.

Devices and systems for performing the methods are a feature of the invention. The devices or systems can include a detection chamber that comprises at least one high efficiency nucleic acid detection array on at least one surface of the chamber. As noted with reference to the methods, the chamber is configured to reduce signal background for signals detected from the array. The device or system typically includes a thermo-regulatory module operably coupled to the detection chamber, which regulates temperature within the chamber during operation of the device. An optical train detects signal(s) produced at the array during operation of the device.

All of the dimensional features of the chamber to reduce background noted with reference to the methods optionally apply to the device. For example, the device can be less than about 500 µm in depth in at least one dimension proximal to the array, e.g., between about 10 µm and about 200 µm in depth in at least one dimension proximal to the array. The chamber surface on which the array is formed can be composed of any suitable material, e.g., a ceramic, glass, quartz, or a polymer. In several embodiments, e.g., those utilizing epi-fluorescence, the surface will be at least partially transparent.

As noted with reference to the methods, the capture nucleic acids on the array are typically present at a non-rate limiting density during operation of the device. The array optionally includes a plurality of capture nucleic acid types, e.g., localized to spatially distinct regions of the array. For example, 5 or more different capture nucleic acid types can be present on the array, e.g., up to about 100 or more different types. The capture nucleic acids are optionally coupled to a thermostable coating on the surface of the chamber, facilitating thermocycling of the array. Example coating can optionally include: a chemically reactive group, an electrophilic group, an NHS ester, a tetra- or pentafluorophenyl ester, a mono- or dinitrophenyl ester, a thioester, an isocyanate, an isothiocyanate, an acyl azide, an epoxide, an aziridine, an aldehyde, an α,β-unsaturated ketone or amide comprising a vinyl ketone or a maleimide, an acyl halide, a sulfonyl halide, an imidate, a cyclic acid anhydride, a group active in a cycloaddition reaction, an alkene, a diene, an alkyne, an azide, or a combination thereof.

The thermo-regulatory module optionally includes features that facilitate thermocycling, such as a thermoelectric module, a Peltier device, a cooling fan, a heat sink, a metal plate configured to mate with a portion of an outer surface of the chamber, etc. Typically, the thermo regulatory module has a feedback enabled control system operably coupled to a computer which controls or is part of the module.

The optical train can include or be operably coupled to an epifluorescent detection system. Typical optical train components include any of: an excitation light source, an arc lamp, a mercury arc lamp, an LED, a lens, an optical filter, a prism, a camera, a photodetector, a CMOS camera, and/or a CCD array. The device can also include or be coupled to an array reader module, which correlates a position of the signal in the array to a nucleic acid to be detected.

The device or system can include or be operably coupled to system instructions, e.g., embodied in a computer or computer readable medium. The instructions can control any aspect of the device or system, e.g., to correlate one or more measurements of signal intensity and a number of amplification cycles performed by the thermo-regulatory module to determine a concentration of a target nucleic acid detected by the device.

A system can include the device, e.g., operably coupled to a computer. The computer can include, e.g., instructions that control thermocycling by the thermo-regulatory module, and/or that specify when images are taken or viewed by the optical train, and/or can convert image information into signal intensity curves as a function of time, determine concentration of a target nucleic acid analyzed by the device, and/or the like. The computer can include instructions for normalizing signal intensity to account for background, e.g., for detecting local background for one or more regions of the array, and for normalizing array signal intensity measurements by correcting for said background. Similarly, the computer can include instructions for normalizing signal intensity by correcting for variability in array capture nucleic acid spotting, uneven field of view of different regions of the array, or the like.

The invention includes, in one aspect, a nucleic acid detection consumable, e.g., for use with the devices and systems of the invention, e.g., to practice the methods of the invention. The consumable can include, e.g., a thin chamber less than about 500 µm in depth, where the chamber includes an optically transparent window that has a high efficiency capture nucleic acid array disposed on an inner surface of the window. The consumable can also include at least one reagent delivery port, e.g., fluidly coupled to the chamber. Typically, the consumable is configured to permit thermocycling of fluid within the chamber.

All of the features noted above with reference to the array and chamber in the context of the devices, systems and methods of the invention apply to the consumable as well (and vice-versa). For example, the nucleic acid array can include a plurality of different capture nucleic acid types, which types are located in spatially distinct regions of the array. The density of the capture nucleic acids can be about, e.g., 2,000 fmol/cm$^2$ or greater, 2,500 fmol/cm$^2$ or greater, 3,000 fmol/cm$^2$ or greater, 4,000 fmol/cm$^2$ or greater, 4,500 fmol/cm$^2$ or greater, or 5,000 fmol/cm$^2$ or greater.

Similarly, the chamber can include a first upper surface comprising the reagent delivery port, and a bottom transparent surface comprising the window, e.g., where the top and bottom surface are joined by sidewalls formed of a pressure-sensitive adhesive material. Other structures for joining the top and bottom surface to form the chamber can also be used. For example, the top and bottom surface can be joined together by a gasket or shaped feature on the upper or lower surface, or both. The gasket or feature is optionally fused or adhered to a corresponding region of the upper or lower surface, or both. In some embodiments, the gasket or feature directs flow of a UV curable adhesive, which adhesive is flowed between the upper and lower surfaces and exposed to UV light, thereby joining the upper and lower surfaces. In other embodiments, the upper and lower surfaces can be ultrasonically fused together, with the gasket or feature delimiting regions that are fused. In another example, the feature is a transparent region on either the upper or lower surface and a corresponding shaded region on a cognate upper or lower surface. In this embodiment, the upper and lower surfaces can be laser welded together by directing laser light through the transparent region and onto the shaded region.

The capture nucleic acid array is typically coupled to a thermally stable coating on the window. For example, the coating can include a chemically reactive group, an electrophilic group, an NHS ester, a tetra- or pentafluorophenyl ester, a mono- or dinitrophenyl ester, a thioester, an isocyanate, an isothiocyanate, an acyl azide, an epoxide, an aziridine, an aldehyde, an α,β-unsaturated ketone or amide comprising a vinyl ketone or a maleimide, an acyl halide, a sulfonyl halide, an imidate, a cyclic acid anhydride, a group active in a cycloaddition reaction, an alkene, a diene, an alkyne, an azide, or a combination thereof. The window itself can include, e.g., glass, quartz, a ceramic, a polymer or other transparent material.

All of the features noted above with respect to the methods, systems and devices apply with respect to the configuration of the chamber in the consumable. For example, the chamber can be between about 10 µm and about 200 µm in depth, e.g., about 140 µm in depth. The chamber can be significantly wider in other dimensions, e.g., between about 1 mm and about 50 mm in average diameter. In one specific embodiment, the chamber is between about 10 mm and about 20 mm in average diameter.

The invention includes kits, e.g., comprising the consumable of the invention. The kits can also include packaging materials, instructions for practicing the methods, control reagents (e.g., control templates, probes, or primers, e.g., which bind to control sites on an array of the consumable).

The methods, systems, devices, consumables and kits can be used in combination, e.g., with the kit providing the consumable for use in a system or device of the invention, e.g., to practice the methods of the invention. Unless stated otherwise, steps of the methods optionally have corresponding structural features in the systems, devices, consumables or kits, and vice-versa.

BRIEF DESCRIPTION OF THE FIGURES

FIGS. 10A and 10B show schematics of aspects of the invention.

DETAILED DESCRIPTION

Figure 1A:
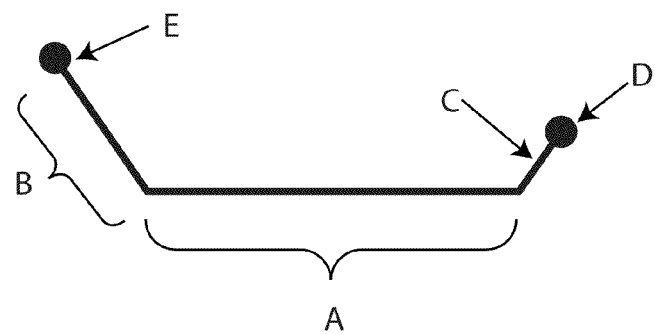
FIGS. 1A and 1B are schematic illustrations of PCR probes of the invention.

Methods of performing target nucleic acid amplification, detection and real-time quantification are a feature of the invention. In the methods, amplification of the target nucleic acid releases a target-specific labeled probe fragment that hybridizes to an array; the array is distributed in the chamber where the amplification takes place. Signal is detected from the array, providing both detection and real-time quantification of the target nucleic acid.

The invention also provides reaction chambers, typically formatted as consumables that comprise nucleic acid detection arrays within the chamber, as well as devices and systems that interact with the consumables.

Methods

The invention provides methods of detecting and quantifying one or more target nucleic acids in a sample, in real time. The methods are highly amenable to multiplexing, enabling specific detection and quantification of a larger number of different target nucleic acids using one chamber reaction and detection than can be achieved using available solution-based real-time nucleic acid detection methods. This is because the invention utilizes array-based detection of analytes (with the array being in contact with the analytes), rather than solution-phase spectral detection. A nucleic acid detection array has significantly greater ability to resolve analytes via array position discrimination as compared to discrimination of, e.g., different dye labels in solution. By way of comparison, it is possible to construct arrays that simultaneously detect thousands of different analytes, while it is typically not possible to detect more than about 5 differently labeled fluorophores in solution.

FIG. 10A provides a partial overview of the method. As shown, a primer 102 is hybridized to a template or target sequence 100 along with a labeled probe 104. The probe 104 comprises a portion 104a that is complementary to the target or template sequence 100, and an orthogonal sequence 104b that is not complimentary to the template (a "flap"), coupled to a label moiety 106. The orthogonal sequence 104b or probe fragment is cleaved during an amplification reaction (e.g., a PCR amplification cycle). In one convenient approach, the natural nuclease activity of a polymerase is used to cleave the flap—in this approach, primer extension by the polymerase results in cleavage of the flap 104b by nuclease action of the polymerase as it encounters the junction between the flap 104b and the template 100. This releases the flap as a labeled probe fragment 104b, which is then hybridized to the array 110 bearing capture probes 112 that are complementary to the released probe fragment 104b, e.g., by adjusting the temperature to conditions that permit specific hybridization. Detection of the label on the array provides for detection and quantification of the template, in real time.

In general, a sample that is to be tested for the presence (or absence) of one or more target nucleic acid(s) is subjected to an amplification reaction. The reaction can easily be multiplexed to amplify, detect and quantify between about 10 and about 100 or more different nucleic acids, in a single reaction chamber. For example, about 10, about 20, about 30, about 40, about 50, about 60, about 70, about 80, about 90, or about 100 or more nucleic acids can be detected in a single amplification/detection chamber. A working example herein demonstrating simultaneous amplification, detection and quantification of 10 different target nucleic acids in a reaction/detection chamber is shown below. This example, and the capabilities of the method herein, exceeds the capabilities of typical spectrally-limited, solution-based multiplex detection.

In the methods, each target nucleic acid to be detected is specifically amplified using at least one, and generally two amplification primers (the use of two primers adds specificity to the reaction, and speeds the rate of product formation, as compared to a single primer). The primers are typically specifically hybridized to the target nucleic acid(s) in the sample, and extended using a polymerase, e.g., in a standard polymerase chain reaction (PCR). The design and construction of amplification primers that can be used to amplify a target nucleic acid of interest follows known methods. For details regarding PCR primer design, see e.g., Anton Yuryev (Editor) (2007) *PCR Primer Design (Methods in Molecular Biology)* [Hardcover] Humana Press; 1st edition ISBN-10: 158829725X, ISBN-13: 978-1588297259, as well as the references noted below.

PCR amplification using the primers on the target template nucleic acids can be performed using appropriate reaction conditions, including use of standard amplification buffers, enzymes, temperatures, and cycle times. For a review of PCR techniques, including hybridization conditions, buffers, reagents, reaction cycle times, and the like, see, e.g., Yuryev (above), van Pelt-Verkuil et al. (2010) *Principles and Technical Aspects of PCR Amplification* Springer; 1st Edition ISBN-10: 9048175798, ISBN-13: 978-9048175796; Bustin (Ed) (2009) *The PCR Revolution: Basic Technologies and Applications* Cambridge University Press; 1st edition ISBN-10: 0521882311, ISBN-13: 978-0521882316; Viljoen et al. (2005) *Molecular Diagnostic PCR Handbook Springer*, ISBN 1402034032; Kaufman et al. (2003) Handbook of Molecular and Cellular Methods in Biology and Medicine Second Edition Ceske (ed) CRC Press (Kaufman); *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; *PCR Protocols A Guide to Methods and Applications* (Innis et al. eds) Academic Press Inc. San Diego, Calif. (1990) (Innis). Amplification conditions, primer design, and other details applicable to real-time based PCR methods are described, e.g., in Logan et al. (eds.) (2009) *Real-Time PCR: Current Technology and Applications*, Caister Academic Press, 1st edition ISBN-10: 1904455395, ISBN-13: 978-1904455394, and M Tevfik Dorak (Editor) (2006) *Real-time PCR (Advanced Methods)* Taylor & Francis, 1st edition ISBN-10: 041537734X ISBN-13: 978-0415377348.

A labeled probe specific for each target nucleic acid in the sample is hybridized along with the amplification primer(s) to the target nucleic acid(s). The amplification reaction cleaves the template-hybridized labeled probe to release a labeled probe fragment. This labeled fragment then hybridizes to the array in the reaction chamber, as shown in FIG. 10A.

FIG. 1A schematically shows a probe useful in the methods of the invention. The probe comprises region A that is complimentary to a target nucleic acid. The probe also comprises "flap" B, which is not complimentary to the target nucleic acid. Label E is attached to flap B. Label E is shown in the terminal position, but the label can, in fact, be formatted at any point along Flap B. For example, any of a variety of nucleotides can be labeled, and used in standard or slightly modified nucleic acid synthesis protocols to provide a label at any desired position on the probe.

In FIG. 1A, Optional region C, comprising label quencher D, is complimentary to a portion of flap B. Under appropriate solution conditions, region C base-pairs with flap B, bringing label E and quencher D into proximity, thereby quenching label E. This reduces signal background of the solution phase in the reaction/detection chamber, but probe quenching is not required for practice of the invention. One surprising aspect of the invention is that it is possible to specifically detect probe fragments bound to the array, even where there is unquenched probe in solution proximal to the array. A working example of this embodiment is described herein. In general, the use of high efficiency arrays in reaction/detection chambers that are configured to reduce solution-phase background permits discrimination of signal at the array from signal background in solution in the methods, consumables, devices and systems of the invention.

Depending upon the assay configuration, a wide variety of different label groups may be employed for labeling the labeled probe. As noted, such labels typically include fluorescent labeling groups, which may include individual fluorophores or interactive dye pairs or groups, e.g., FRET pairs, as well as donor/quencher pairs. A range of different fluorescent labeling groups suitable for labeling nucleic acid probes are described in, e.g., the Molecular Probes Handbook, 11$^{th}$ Edition (Life Technologies, Inc.).

While much of the discussion herein is directed to PCR based amplification, other amplification reactions can be substituted. For example, multienzyme systems involving cleavage reactions coupled to amplification reactions, such as those including the cleavage of scissile bonds (see, e.g., U.S. Pat. No. 5,011,769; U.S. Pat. No. 5,660,988; U.S. Pat. No. 5,403,711; U.S. Pat. No. 6,251,600) and forked nucleic acid structures (U.S. Pat. No. 7,361,467; U.S. Pat. No. 5,422,253; U.S. Pat. No. 7,122,364; U.S. Pat. No. 6,692,917) can be used. Helicase dependent amplification coupled to TaqMan like cleavage (Tong, Y et. al 2008 BioTechniques 45:543-557) can also be used. Nucleic acid sequence based amplification (NASBA), or the ligase chain reaction (LCR) can be used. In NASBA-based approaches, the probe can be hybridized to a template along with amplification primer(s), as in PCR. The probe can be cleaved by the nuclease action of reverse transcriptase, or an added endonuclease, releasing the probe fragment in a manner similar to the release by a polymerase in PCR. One potential advantage of NASBA is that no thermocycling is required. This simplifies overall device and system requirements. For a description of NASBA, see, e.g., Compton (1991), "Nucleic acid sequence-based amplification," Nature 350 (6313): 91-2. For the use of NASBA to detect, e.g., pathogenic nucleic acids, see, e.g., Keightley et al. (2005) "Real-time NASBA detection of SARS-associated coronavirus and comparison with real-time reverse transcription-PCR," *Journal of Medical Virology* 77 (4): 602-8. When an LCR-style reaction is used, the probe can be cleaved using an endonuclease, rather than relying on nuclease activity of the amplification enzyme.

In the methods herein, a detection chamber that has at least one high efficiency nucleic acid detection array on at least one inner surface of the chamber is provided. The high efficiency array typically has a non-rate limiting number of capture nucleic acids that permits an efficient capture of probe fragments produced by the amplification reaction in the chamber. The capture nucleic acids are configured to capture relatively small probe nucleic acids, which also increases array efficiency. The chamber is configured to reduce signal background proximal to the array, e.g., by shaping the chamber to reduce background. For example, background is reduced by making the chamber thin (shallow) proximal to (e.g., above or below) the array; e.g., the chamber is typically about 500 μm or shallower above or below the array, although detection in chambers as deep as 1 mm or larger can work. Further details regarding the reaction chamber and array is described below with reference to the consumable useful in the methods.

Signals captured by the array are detected and signal intensity is measured. Signal intensity is correlated to the presence and/or quantity of the target nucleic acid present in the sample. Typically, the sample is amplified for more than 1 cycle before initial detection, to increase the level of signal by increasing the number of probe fragments released by the amplification. For example, the target nucleic acid can optionally be amplified for at least, e.g., 2, 3, 4, 5, 6, 7, 8, 9, 10 or more amplification cycles prior to detecting signal from the array.

FIG. 10B provides an alternative configuration of the assays of the invention. As shown, the target specific probe is again provided with an orthogonal flap portion 104$b$, as noted in FIG. 10A, above. However, rather than being labeled with a fluorescent labeling moiety 106 as in FIG. 10A, that produces a fluorescent signal, the flap 104$b$ bears a quencher group 116. In contrast, the capture probe 112 on the array 110 is labeled with a corresponding fluorescent group 114, i.e., that is quenched by the quencher group 116 on the flap 104$b$. When the flap portion 104$b$ is cleaved and released from the full length probe 104 upon amplification of the target sequence 100, the flap is able to hybridize to the capture probe 112 and quenches the signal from its associated fluorophore 114. As a result, presence of a target sequence of interest, results in amplification of that sequence and cleavage of the quencher-flap 104$b$ from the probe 104, which in turn, is able to hybridize to the capture probe 112 on the array 110, resulting in a reduced or absent fluorescent signal for a given capture probe location on the array. By locating the quencher and fluorophore on complementary portions of the flap or probe fragment and capture probe, respectively, one can ensure that these groups are within sufficient proximity for energy transfer and quenching.

Fluorophore-quencher group pairs that may be coupled to the flap and capture probes are well known in the art, for example, fluorophore-quencher pairs such as black hole quencher 2/Cy 3 and Iowa Black RQ/Cy3.

As will be appreciated, the foregoing quencher probe assay configuration eliminates a fluid borne fluorescent component and consequently, any background fluorescent signal that might emanate from the fluid. Instead, the signaling event is the loss of fluorescent signal due to quenching of surface bound fluorophores.

In one typical embodiment, fluorescent or other optical images are captured from the array at selected times, temperatures, and amplification cycle intervals, during the amplification reactions. These images are analyzed to determine whether the target nucleic acid(s) are present in the sample, and to provide quantification of starting target nucleic acid concentrations in the sample. The images are analyzed using a combination of mean gray intensity measurements, background correction and baseline adjustments. The background can be measured locally for each spot in the array. The background is computed by measuring the image intensity of a concentric annulus of the solution surrounding the array region (e.g., array spot) of interest. The signal from each region is then corrected to account for local background in the region. The corrected signal from each region can be further normalized to account for variability in spotting, as well as uneven illumination in the field of view. The average of the corrected intensity measurements obtained from the first few cycles, typically between cycle 5 and 15, are used to adjust the baseline and normalize measurements from each region.

Further details regarding methods of quantifying nucleic acids based upon signal intensity measurements following amplification can be found, e.g., in the references noted in above this section and in Jang B. Rampal (Editor) (2010)

*Microarrays: Volume 2, Applications and Data Analysis (Methods in Molecular Biology)* Humana Press; 2nd Edition ISBN-10: 1617378526, ISBN-13: 978-1617378522; Stephen A. Bustin (Editor) (2004) *A-Z of Quantitative PCR (IUL Biotechnology, No. 5) (IUL Biotechnology Series)* International University Line; 1st edition ISBN-10: 0963681788, ISBN-13: 978-0963681782; and in Kamberova and Shah (2002) *DNA Array Image Analysis: Nuts & Bolts (Nuts & Bolts series)* DNA Press; 2nd edition ISBN-10: 0966402758, ISBN-13: 978-0966402759.

In an alternate configuration, the capture probes may optionally be coupled to a mobile substrate, such as beads, resins, particles or the like (generally referred to interchangeably herein as "beads"), rather than a static substrate. For example, as noted elsewhere herein, a planar substrate may be used to provide arrayed capture probes that will hybridize with the cleaved probe fragments produced during the amplification of the target nucleic acid sequence or sequences within the sample material. The presence of a given target nucleic acid sequence is detected by detecting which capture probe position on the array the probe fragments hybridize. Because each probe fragment is specific to a particular target sequence, if that probe fragment is present, it is indicative that the target was present and amplified. In a mobile phase substrate, each different type of capture probe in a given analysis is coupled to a different mobile substrate that also bears a unique label. The mobile substrates are then passed through a detection channel in order to identify both the bead, and by implication, the capture probe, and whether the labeled probe fragment is present. If the labeled probe is detected on a given bead that corresponds to a particular capture probe, it is indicative that the target sequence associated with that probe fragment (and complementary capture probe) was present in the sample and amplified. This aspect of the invention may be employed in endpoint detection, e.g., after completion of the overall amplification reaction, but may also be employed in quantitative analysis, e.g., siphoning a fraction of beads from the amplification mixture after one or more amplification cycles, and measuring the labeled probe fragment signal intensity from the beads.

The concentration of captured labeled probe fragments on a given bead will provide a sufficiently high signal to background ratio in the detection channel such that separation of the beads from the reaction mixture is not necessary. In addition, as with the array based substrates, the inclusion of a secondary structure in the intact probe and/or optional quenching group permits greater ability to distinguish between probe fragment and intact probe background signal, whether in solution or from unintended binding to the mobile substrate. In some cases, the nature of the intact probe's secondary structure would also be expected to give rise to steric hindrance in binding with the capture probes on the mobile substrate, resulting in some cases in a reduced likelihood that the intact probe would bind to the beads.

A variety of different bead types may be used in conjunction with this aspect of the invention. For example, polystyrene, cellulosic, acrylic, vinyl, silica, paramagnetic or other inorganic particles, or any of a variety of other bead types may be employed. As noted, the beads with typically be differentially labeled with a unique label signature. Again, a variety of different label types may be used, including organic fluorescent labels, inorganic fluorescent labels (e.g., quantum dots), luminescent labels, electrochemical labels, or the like. Such labels are widely commercially available and configured to be readily coupled to appropriately activated beads. In the case of fluorescent labeling groups, a large number of label signatures may be provided by providing different combinations of 2, 3, 4 or more spectrally distinct fluorescent labeling groups and different levels of each label, so as to provide a broad range of unique label signatures without having to use a broad spectrum of excitation radiation, e.g., multiple lasers.

The method is typically performed using the devices, systems, consumables and kits herein. All features of the devices, systems and consumables can be provided to practice the methods herein, and the methods herein can be practiced in combination with the devices, systems, consumables and kits.

Consumables

The one-pot reaction chambers of the invention are configured to reduce signal background. High-efficiency arrays are formed on at least one inner surface of the chambers. The arrays typically are in contact with amplification reactants and products during both amplification and array hybridization steps of the methods. This allows a user to run one or more amplification reaction cycles, detect the results by monitoring signal from the array in real time, and to then run one or more additional amplification cycles, again followed by detection. Thus, signal intensity from the array can be used to both detect and quantify a nucleic acid of interest, in real time.

The consumables of the invention include a chamber and a high efficiency array on an inner surface of the chamber. The chamber is typically thin (shallow), e.g., less than about 1 mm in depth. In general, the thinner the chamber, the less solution above the array, which reduces signal background from labeled probes or probe fragments in the solution. Typical desirable chamber depths are in the range of about 1 µm to about 500 µm. For ease of fabrication of the consumable, the chamber is often in the range of about 10 µm to about 250 µm in depth above the array, e.g., about 100 µm to about 150 µm in depth. The chamber can include a surface that has a reagent delivery port, e.g., for delivery of a sample by manual or automated pipettor.

Figure 2:
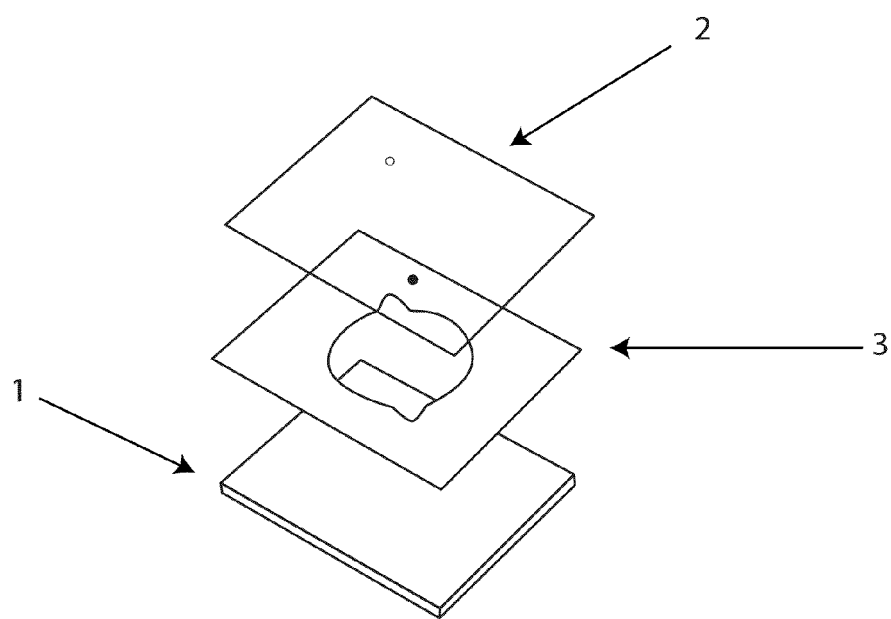
FIG. 2 is a schematic of a PCR chamber of the invention.

FIG. 2 provides a blow-up schematic of an example consumable. In this example, bottom surface layer 1 and upper surface layer 2, are joined by middle layer 3. Cutout 4 forms a chamber upon assembly of layers 1, 2, and 3. Port(s) 5 form(s) a convenient way to deliver buffer and reagents to the chamber upon assembly. A high efficiency array can be formed on the top or bottom layer in the region that forms the top or bottom surface of the cutout. In one convenient embodiment, where epifluorescent detection is used for detection of label bound to the array, the array is fabricated on the lower surface, with the consumable being configured to be viewed by detection optics located in the devices and systems of the invention below the lower surface. Generally, either the top or bottom surface (or both) will include a window through which detection optics can view the array.

Middle layer 3 can take any of a variety of forms, depending on the consumable assembly method to be used. In one convenient embodiment, top and bottom surfaces 1 and 2 are joined by layer 3 formed of a pressure-sensitive adhesive material. Pressure sensitive adhesive layers (e.g., tape) are well known and widely available. See, e.g., Benedek and Feldstein (Editors) (2008) *Handbook of Pressure-Sensitive Adhesives and Products:* Volume 1: *Fundamentals of Pressure Sensitivity*, Volume 2: *Technology of Pressure-Sensitive Adhesives and Products*, Volume 3: *Applications of Pressure-Sensitive Products*, CRC Press; 1st edition ISBN-10: 1420059343, ISBN-13: 978-1420059342.

Other fabrication methods for joining the top and bottom surface to form the chamber can also be used. For example, the top and bottom surfaces can be joined together by a gasket or shaped feature on the upper or lower surface, or both. The gasket or feature is optionally fused or adhered to a corresponding region of the upper or lower surface, or both. Silicon and polymer chip fabrication methods can be applied to form features in the top or bottom surface. For an introduction to feature fabrication methods, including micro-feature fabrication, see, e.g., Franssila (2010) *Introduction to Microfabrication* Wiley; 2nd edition ISBN-10: 0470749830, ISBN-13: 978-0470749838; Shen and Lin (2009) "Analysis of mold insert fabrication for the processing of microfluidic chip" *Polymer Engineering and Science* Publisher: Society of Plastics Engineers, Inc. Volume: 49 Issue: 1 Page: 104(11); Abgrall (2009) *Nanofluidics* ISBN-10: 159693350X, ISBN-13: 978-1596933507; Kaajakari (2009) *Practical MEMS: Design of microsystems, accelerometers, gyroscopes, RF MEMS, optical MEMS, and microfluidic systems* Small Gear Publishing ISBN-10: 0982299109, ISBN-13: 978-0982299104; Saliterman (2006) *Fundamentals of BioMEMS and Medical Microdevices* SPIE Publications ISBN-10: 0819459771, ISBN-13: 978-0819459770; Madou (2002) *Fundamentals of Microfabrication: The Science of Miniaturization*, Second Edition CRC Press; ISBN-10: 0849308267, ISBN-13: 978-0849308260. These fabrication methods can be used to form essentially any feature that is desired on the top or bottom surface, eliminating the need for an intermediate layer. For example, a depression can be formed in the top or bottom surface (or both) and the two layers joined, thereby forming the chamber.

In some embodiments, the gasket or feature directs flow of a UV or radiation curable adhesive. This adhesive is flowed between the upper and lower surfaces and exposed to UV light or radiation (e.g., electron beam, or "EB" radiation), thereby joining the upper and lower surfaces. For a description of available adhesives, including UV and radiation curable adhesives, see, e.g., Ebnesajjad (2010) *Handbook of Adhesives and Surface Preparation: Technology, Applications and Manufacturing* William Andrew; 1st edition ISBN-10: 1437744613, ISBN-13: 978-1437744613; Drobny (2010) *Radiation Technology for Polymers, Second Edition* CRC Press; 2 edition ISBN-10: 1420094041, ISBN-13: 978-1420094046.

In other embodiments, the upper and lower surfaces can be ultrasonically fused together, with the gasket or surface feature delimiting regions that are fused and the chamber or other structural features to be produced in the consumable. Ultrasonic welding and related techniques useful for fusing materials are taught, e.g., in Astashev and Babitsky (2010) *Ultrasonic Processes and Machines: Dynamics, Control and Applications* (Foundations of Engineering Mechanics) Springer; 1st Edition. edition ISBN-10: 3642091245, ISBN-13: 978-3642091247; and Leaversuch (2002) "How to use those fancy ultrasonic welding controls," *Plastics Technology* 48(10): 70-76.

In another example, the feature is a transparent region on either the upper or lower surface and a corresponding shaded region on a cognate upper or lower surface. In this embodiment, the upper and lower surfaces can be laser welded together by directing laser light through the transparent region and onto the shaded region. Laser welding methods are taught, e.g., in Steen et al. (2010) *Laser Material Processing* Springer; 4th ed. edition ISBN-10: 1849960615, ISBN-13: 978-1849960618; Kannatey-Asibu (2009) *Principles of Laser Materials Processing* (Wiley Series on Processing of Engineering Materials) Wiley ISBN-10: 0470177985, ISBN-13: 978-0470177983; and Duley (1998) *Laser Welding* Wiley-Interscience ISBN-10: 0471246794, ISBN-13: 978-0471246794.

The capture nucleic acid array is typically coupled to a thermally stable coating on the window. The window itself can include, e.g., glass, quartz, a ceramic, a polymer or other transparent material. A variety of coatings suitable for coating the window are available. In general, the coating is selected based upon compatibility with the array substrate (e.g., whether the chamber surface that the array is attached to is glass or a polymer), ability to be derivatized or treated to include reactive groups suitable for attaching array members, and compatibility with process conditions (e.g., thermostability, photostability, etc.). For example, the coating can include a chemically reactive group, an electrophilic group, an NHS ester, a tetra- or pentafluorophenyl ester, a mono- or dinitrophenyl ester, a thioester, an isocyanate, an isothiocyanate, an acyl azide, an epoxide, an aziridine, an aldehyde, an $\alpha,\beta$-unsaturated ketone or amide comprising a vinyl ketone or a maleimide, an acyl halide, a sulfonyl halide, an imidate, a cyclic acid anhydride, a group active in a cycloaddition reaction, an alkene, a diene, an alkyne, an azide, or a combination thereof. For a description of surface coatings and their use in attaching biomolecules to surfaces see, e.g., Plackett (Editor) (2011) *Biopolymers: New Materials for Sustainable Films and Coatings* Wiley ISBN-10: 0470683414, ISBN-13: 978-0470683415; Niemeyer (Editor) (2010) *Bioconjugation Protocols: Strategies and Methods (Methods in Molecular Biology)* Humana Press; 1st Edition. edition ISBN-10: 1617373540, ISBN-13: 978-1617373541; Lahann (Editor) (2009) *Click Chemistry for Biotechnology and Materials Science* Wiley ISBN-10: 0470699701, ISBN-13: 978-0470699706; Hermanson (2008) *Bioconjugate Techniques, Second Edition* Academic Press; 2nd edition ISBN-10: 0123705010, ISBN-13: 978-0123705013. Wuts and Greene (2006) *Greene's Protective Groups in Organic Synthesis* Wiley-Interscience; 4th edition ISBN-10: 0471697540, # ISBN-13: 978-0471697541; Wittmann (Editor) (2006) *Immobilisation of DNA on Chips II* (Topics in Current Chemistry) Springer; 1st edition ISBN-10: 3540284362, ISBN-13: 978-3540284369; Licari (2003) *Coating Materials for Electronic Applications: Polymers, Processing, Reliability, Testing (Materials and Processes for Electronic Applications)* William Andrew ISBN-10: 0815514921, ISBN-13: 978-0815514923; Conk (2002) *Fabrication Techniques for Micro-Optical Device Arrays* Storming Media ISBN-10: 1423509641, ISBN-13: 978-1423509646, and Oil and Colour Chemists' Association (1993) *Surface Coatings—Raw materials and their usage, Third Edition* Springer; 3rd edition, ISBN-10: 0412552108, ISBN-13: 978-0412552106.

Methods of making nucleic acid arrays are available and can be adapted to the invention by forming the arrays on an inner chamber surface. Techniques for forming nucleic acid microarrays that can be used to form arrays on an inner chamber surface are described, e.g., in Rampal (Editor) *Microarrays: Volume I: Synthesis Methods (Methods in Molecular Biology)* Humana Press; 2nd Edition ISBN-10: 1617376639, ISBN-13: 978-1617376634; Müller and Nicolau (Editors) (2010) *Microarray Technology and Its Applications (Biological and Medical Physics, Biomedical Engineering)* Springer; 1st Edition. ISBN-10: 3642061826, ISBN-13: 978-3642061820; Xing and Cheng (Eds.) (2010) *Biochips: Technology and Applications (Biological and Medical Physics, Biomedical Engineering)* Springer; 1st Edition. ISBN-10: 3642055850, ISBN-13: 978-3642055850; Dill et al. (eds) (2010) *Microarrays: Preparation, Microfluidics, Detection Methods, and Biological Applications (Integrated Analytical Systems)* Springer ISBN-10: 1441924906, ISBN-13: 978-1441924902; Whittmann (2010) *Immobilisation of DNA on Chips II (Topics in Current Chemistry)* Springer; 1st Edition ISBN-10: 3642066666, ISBN-13: 978-3642066665; Rampal (2010) *DNA Arrays: Methods and Protocols (Methods in*

Molecular Biology) Humana Press; 1st Edition ISBN-10: 1617372048, ISBN-13: 978-1617372049; Schena (Author, Editor) (2007) *DNA Microarrays (Methods Express)* Scion Publishing; 1st edition, ISBN-10: 1904842151, ISBN-13: 978-1904842156; Appasani (Editor) (2007) *Bioarrays: From Basics to Diagnostics* Humana Press; 1st edition ISBN-10: 1588294765, ISBN-13: 978-1588294760; and Ulrike Nuber (Editor) (2007) *DNA Microarrays (Advanced Methods)* Taylor & Francis ISBN-10: 0415358663, ISBN-13: 978-0415358668. Techniques for attaching DNA to a surface to form an array can include any of a variety of spotting methods, use of chemically reactive surfaces or coatings, light-directed synthesis, DNA printing techniques, and many other methods available in the art.

Methods of quantifying array densities are provided in the references noted above and in Gong et al. (2006) "Multi-technique Comparisons of Immobilized and Hybridized Oligonucleotide Surface Density on Commercial Amine-Reactive Microarray Slides" *Anal. Chem.* 78:2342-2351.

The consumable can be packaged in a container or packaging materials to form a kit. The kit can also include components useful in using the consumable, e.g., control reagents (e.g., a control template, control probe, control primers, etc.), buffers, or the like.

Devices and Systems

Devices and systems that use the consumable and/or practice the methods of the invention are a feature of the invention as well. The device or system can include the features of the consumable, e.g., a reaction chamber and array (whether formatted as a consumable, or as dedicated portion of the device). Most typically, the device will typically have a receiver, e.g., a stage that mounts the consumable noted above, along with detection optics for monitoring the array, modules for thermocycling the chamber, and a computer with system instructions that control thermocycling, detection, and post-signal processing.

Figure 11:
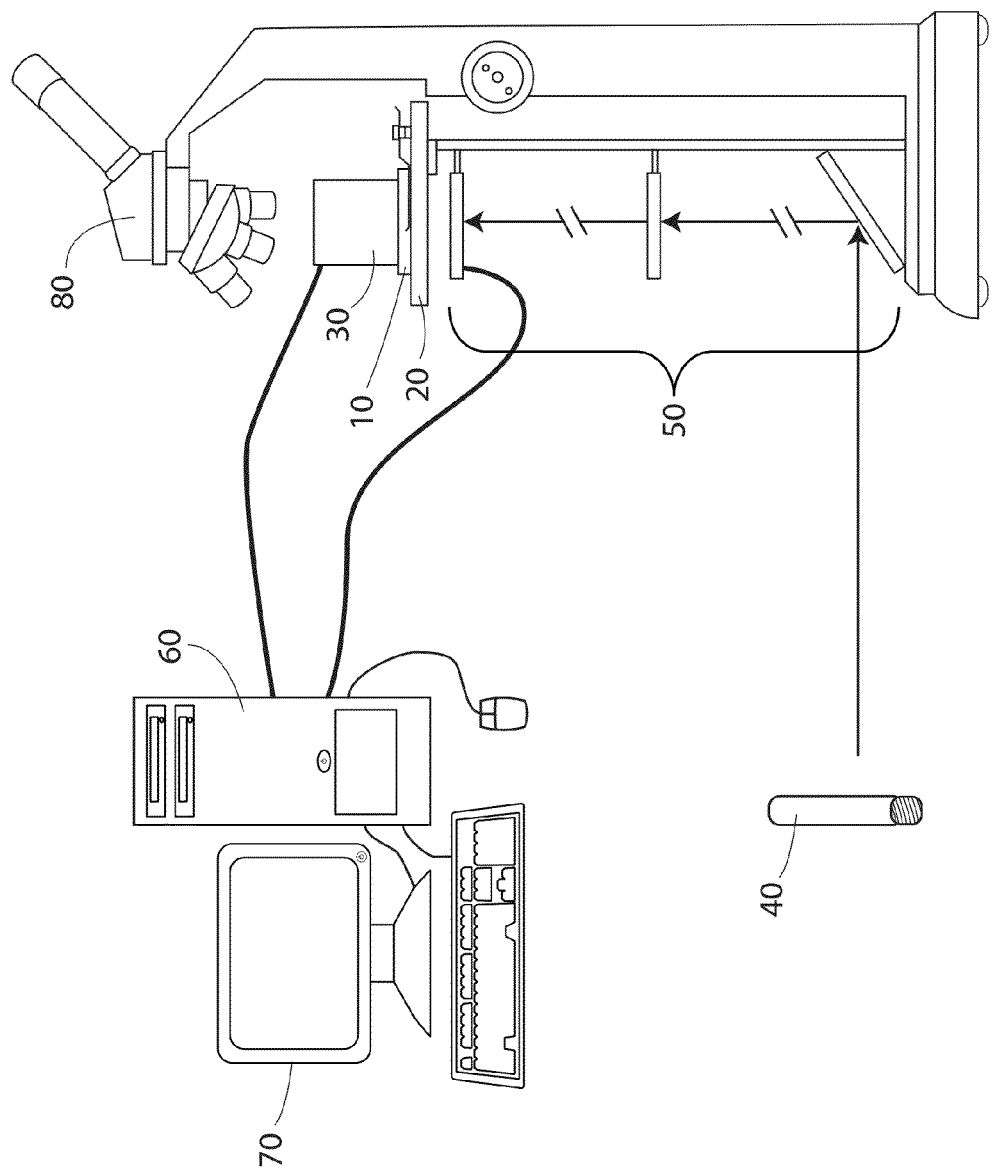
FIG. 11 is a schematic system illustration.

An example schematic system is illustrated in FIG. 11. As shown, consumable 10 is mounted on stage 20. Environmental control module (ECM) 30 (e.g., comprising a Peltier device, cooling fans, etc.) provides environmental control (e.g., thermocycling of temperature). Illumination light is provided by source 40 (e.g., a lamp, arc lamp, LED, laser, or the like). Optical train 50 directs light from illumination source 40 to consumable 10. Signals from consumable 10 are detected by the optical train and signal information is transmitted to computer 60. Computer 60 optionally also controls ECM 30 Signal information can be processed by computer 60, and outputted to user viewable display 70, or to a printer, or both. ECM 30 can be mounted above or below consumable 10 and additional viewing optics 80 (located above or below stage 20) can be included.

The stage/receiver is configured to mount the consumable for thermocycling and analysis. The stage can include registration and alignment features such as alignment arms, detents, holes, pegs, etc., that mate with corresponding features of the consumable. The stage can include a cassette that receives and orients the consumable, placing it in operable linkage with other device elements, although this is not necessary in many embodiments, e.g., where the consumable mounts directly to the stage. Device elements are configured to operate with the consumable and can include a fluidic delivery system for delivering buffers and reagents to the consumable, a thermocycling or other temperature control or environmental control module, detection optics, etc. In embodiments where the chamber is build into the device, rather being incorporated into the consumable, the device elements are typically configured to operate on or proximal to the chamber.

Fluid delivery to the consumable can be done by the device or system, or can be performed prior to loading the consumable into the device or system. Fluid handling elements can be integrated into the device or system, or can be formatted into a separate processing station discrete from the device or system. Fluid handling elements can include pipettors (manual or automated) that deliver reagents or buffers to ports in the consumable, or can include capillaries, microfabricated device channels, or the like. Manual and automated pipettors and pipettor systems that can be used to load the consumable are available from a variety of sources, including Thermo Scientific (USA), Eppendorf (Germany), Labtronics (Canada) and many others. Generally speaking, a variety of fluidic handling systems are available and can be incorporated into the devices and systems of the invention. See, e.g., Kirby (2010) *Micro-and Nanoscale Fluid Mechanics: Transport in Microfluidic Devices* ISBN-10: 0521119030, ISBN-13: 978-0521119030; Bruus (2007) *Theoretical Microfluidics (Oxford Master Series in Physics)* Oxford University Press, USA ISBN-10: 0199235090, ISBN-13: 978-0199235094; Nguyen (2006) *Fundamentals And Applications of Microfluidics, Second Edition (Integrated Microsystems)* ISBN-10: 1580539726, ISBN-13: 978-1580539722; Wells (2003) *High Throughput Bioanalytical Sample Preparation: Methods and Automation Strategies (Progress in Pharmaceutical and Biomedical Analysis)* Elsevier Science; 1st edition ISBN-10: 044451029X, ISBN-13: 978-0444510297. The consumable optionally comprises ports that are configured to mate with the delivery system, e.g., ports of an appropriate dimension for loading by a pipette or capillary delivery device.

The ECM or thermo-regulatory module can include features that facilitate thermocycling, such as a thermoelectric module, a Peltier device, a cooling fan, a heat sink, a metal plate configured to mate with a portion of an outer surface of the chamber, a fluid bath, etc. Many such thermo-regulatory components are available for incorporation into the devices and systems of the invention. See, for example, Kennedy and Oswald (Editors) (2011) *PCR Troubleshooting and Optimization: The Essential Guide*, Caister Academic Press ISBN-10: 1904455727; ISBN-13: 978-1904455721; Bustin (2009) *The PCR Revolution: Basic Technologies and Applications* Cambridge University Press; 1st edition ISBN-10: 0521882311, ISBN-13: 978-0521882316; Wittwer et al. (eds.) (2004) *Rapid Cycle Real-Time PCR-Methods and Applications* Springer; 1 edition, ISBN-10: 3540206299, ISBN-13: 978-3540206293; Goldsmid (2009) Introduction to Thermoelectricity (Springer Series in Materials Science) Springer; 1st edition, ISBN-10: 3642007155, ISBN-13: 978-3642007156; Rowe (ed.) (2005) *Thermoelectrics Handbook Macro to Nano* CRC Press; 1 edition, ISBN-10: 0849322642, ISBN-13: 978-0849322648. The thermo regulatory module can, e.g., be formatted into a cassette that receives the consumable, or can be mounted on the stage in operable proximity to the consumable.

Typically, the ECM or thermo regulatory module has a feedback enabled control system operably coupled to a computer which controls or is part of the module. Computer directed feedback enabled control is an available approach to instrument control. See, e.g., Tooley (2005) *PC Based Instrumentation and Control, Third Edition*, ISBN-10: 0750647167, ISBN-13: 978-0750647168; Dix et al. (2003) *Human-Computer Interaction (3rd Edition)* Prentice Hall, 3rd edition ISBN-10: 0130461091, ISBN-13:

978-0130461094. In general, system control is performed by a computer, which can use, e.g., a script file as an input to generate target temperatures and cycle time periods as well as to specify when images are to be viewed/taken by the detection optics. Photo images are typically taken at different times during a reaction and are analyzed by the computer to generate intensity curves as a function of time and thereby derive the concentration of the target.

The optical train can include any typical optical train components, or can be operably coupled to such components. The optical train directs illumination to the consumable, e.g., focused on an array of the consumable, or an array region. The optical train can also detect light (e.g., a fluorescent or luminescent signal) emitted from the array. For a description of available optical components, See, e.g., Kasap et al. (2009) *Cambridge Illustrated Handbook of Optoelectronics and Photonics Cambridge University Press;* 1st edition ISBN-10: 0521815967, ISBN-13: 978-0521815963; Bass et al. (2009) *Handbook of Optics, Third Edition Volume I: Geometrical and Physical Optics, Polarized Light, Components and Instruments(set)* McGraw-Hill Professional; 3rd edition, ISBN-10: 0071498893, ISBN-13: 978-0071498890; Bass et al. (2009) *Handbook of Optics, Third Edition Volume II: Design, Fabrication and Testing, Sources and Detectors, Radiometry and Photometry* McGraw-Hill Professional; 3rd edition ISBN-10: 0071498907, ISBN-13: 978-0071498906; Bass et al. (2009) *Handbook of Optics, Third Edition Volume III: Vision and Vision Optics* McGraw-Hill Professional, ISBN-10: 0071498915, ISBN-13: 978-0071498913; Bass et al. (2009) *Handbook of Optics, Third Edition Volume IV: Optical Properties of Materials, Nonlinear Optics, Quantum Optics* McGraw-Hill Professional, 3rd edition, ISBN-10: 0071498923, ISBN-13: 978-0071498920; Bass et al. (2009) *Handbook of Optics, Third Edition Volume V: Atmospheric Optics, Modulators, Fiber Optics, X-Ray and Neutron Optics* McGraw-Hill Professional; 3rd edition, ISBN-10: 0071633138, ISBN-13: 978-0071633130; and Gupta and Ballato (2006) *The Handbook of Photonics, Second Edition,* CRC Press, 2nd edition ISBN-10: 0849330955, ISBN-13: 978-0849330957. Typical optical train components include any of: an excitation light source, an arc lamp, a mercury arc lamp, an LED, a lens, an optical filter, a prism, a camera, a photodetector, a CMOS camera, and/or a CCD array. In one desirable embodiment, an epifluorescent detection system is used. The device can also include or be coupled to an array reader module, which correlates a position of the signal in the array to a nucleic acid to be detected.

In the context of the mobile substrate embodiments of the invention, in certain aspects, the reaction vessel may be coupled directly to a detection channel, e.g., within an integrated microfluidic channel system, or through an appropriate fluidic interface between the amplification mixture and the detection channel. Alternatively, a fluidic interface, such as are present in conventional flow cytometers, may be provided on the detection channel in order to sample the amplification reaction mixture. The detection channel is typically configured to have a dimension that permits substantially only single beads to traverse the channel at a given time. The detection channel will typically include a detection window allowing excitation of the beads and collection of the fluorescent signals emanating from the beads. In many cases, a fused silica or glass capillary or other transparent microfluidic channel is used as the detection channel.

The optical detection systems of the invention will typically include one or more excitation light sources capable of delivering excitation light at one or more excitation wavelengths. Also included will be an optical train that is configured to collect the light emanating from the detection channel, and filter excitation light from the fluorescent signals. The optical train also typically includes additional separation elements for transmitting the fluorescent signals, and for separating the fluorescent signal component(s) emanating from the bead and the signal component(s) emanating from the captured probe fragment.

Figure 14:
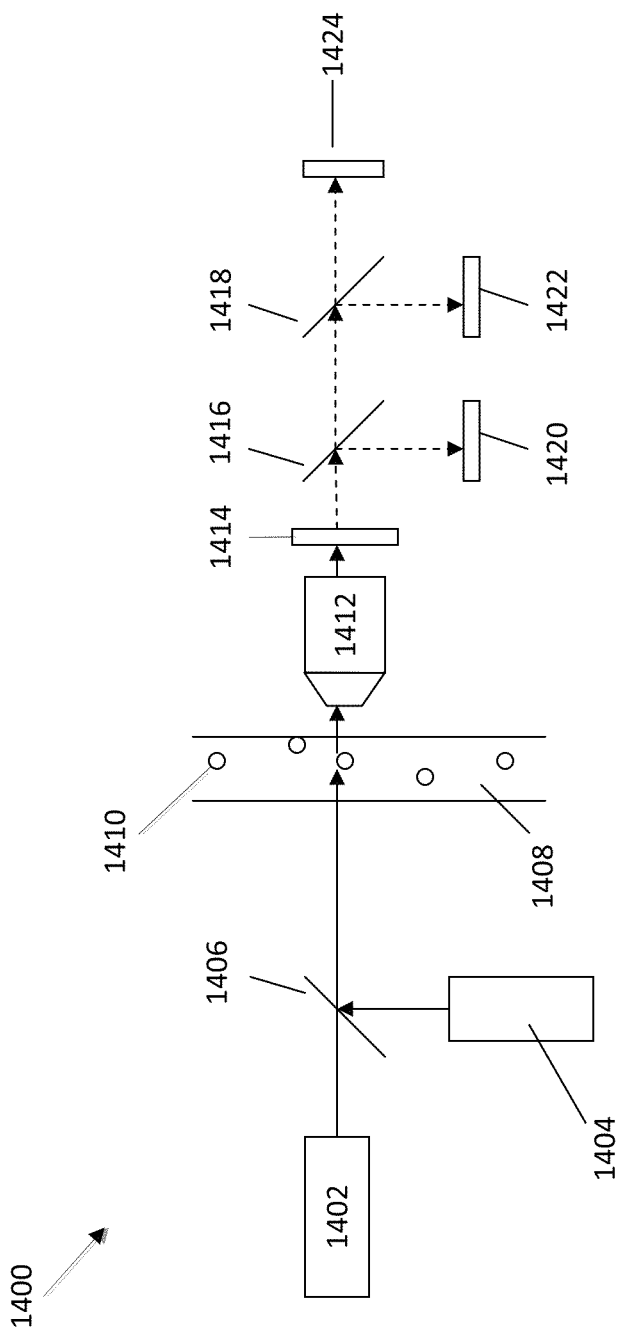
FIG. 14 is a schematic illustration of an overall detection system for mobile substrate embodiments of the invention.

FIG. 14 provides a schematic illustration of an overall detection system 1400. As shown, the system includes first and second excitation light sources, such as lasers 1402 and 1404, that each provide excitation light at different wavelengths. Alternatively, a single broad spectrum light source or multiple narrow spectrum light sources may be used to deliver excitation light at the appropriate wavelength range or ranges to excite the detectable labels in the sample, e.g., those associated with the beads, and those associated with the labeled probe fragments.

Excitation beams, shown as the solid arrows, from each laser are directed to the detection channel 1408, e.g., through the use of directional optics, such as dichroic 1406. Light that emanates from the beads 1410 in the detection channel 1408, is collected by collection optics, e.g., objective lens 1412. The collected light is then passed through filter 1414 that is configured to pass the emitted fluorescence, shown as the dashed arrows, while rejecting the collected excitation radiation. The collected fluorescence includes fluorescence emitted from the label on the captured probe fragments at a first emission spectrum, as well as fluorescent signals from the bead label signature, at one or more different emission spectra, depending upon the number of labels used in the beads. The collected fluorescence is then passed through dichroic 1416 that reflects the fluorescence from the captured probe fragments to a first detector 1420. The remaining fluorescent signature from the beads is then subjected to further separation by passing the signal through a second dichroic 1418, that reflects a first bead signal component to a second detector 1422, and passes a second bead signal component to the third detector 1424. The detectors are typically coupled to an appropriate processor or computer for storing signal data associated with detected beads, and analyzing the signal data to determine the identity of the bead, and thus the capture probe and associated target nucleic acid sequence. Additionally, the processor or computer may include programming to quantify signal data and originating target sequence copy number, where time course experiments are performed, e.g., beads are sampled after one or more amplification cycles in an overall amplification reaction.

The device or system can include or be operably coupled to system instructions, e.g., embodied in a computer or computer readable medium. The instructions can control any aspect of the device or system, e.g., to correlate one or more measurements of signal intensity and a number of amplification cycles performed by the thermo-regulatory module to determine a concentration of a target nucleic acid detected by the device.

A system can include a computer operably coupled to the other device components, e.g., through appropriate wiring, or through wireless connections. The computer can include, e.g., instructions that control thermocycling by the thermo-regulatory module, e.g., using feedback control as noted above, and/or that specify when images are taken or viewed by the optical train. The computer can receive or convert image information into digital information and/or signal intensity curves as a function of time, determine concentration of a target nucleic acid analyzed by the device, and/or the like. The computer can include instructions for normalizing signal intensity to account for background, e.g., for detecting local background for one or more regions of the array, and for normalizing array signal intensity measurements by correcting for said background. Similarly, the computer can include instructions for normalizing signal intensity by correcting for variability in array capture nucleic acid spotting, uneven field of view of different regions of the array, or the like.

Additional Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" e.g., of the consumable chamber discussed herein, optionally includes a combination of two or more surfaces, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology is used in accordance with the definitions set out below.

An "amplification primer" is a moiety (e.g., a molecule) that can be extended in a template-dependent amplification reaction. Most typically, the primer will include or will be a nucleic acid that binds to the template under amplification conditions. Typically, the primer will comprise a terminus that can be extended by a polymerase (e.g., by a thermostable polymerase in a polymerase chain reaction), or by a ligase (e.g., as in a ligase chain reaction).

A "detection chamber" is a partly or fully enclosed structure in which a sample is analyzed or a target nucleic acids is detected. The chamber can be entirely closed, or can include ports or channels fluidly coupled to the chamber, e.g., for the delivery of reagents or reactants. The shape of the chamber can vary, depending, e.g., on the application and available system equipment. A chamber is "configured to reduce signal background proximal to the array" when it is dimensionally shaped to reduce signal background, e.g., by including a narrow dimension (e.g., chamber depth) near the array (thereby reducing the amount of solution-generated signal proximal to the array), or when the chamber is otherwise configured to reduce background, e.g., by the use of coatings (e.g., optical coatings) or structures (e.g., baffles or other shaped structures proximal to the array). Typically, the chamber is configured to have a dimension (e.g., depth) proximal to the array, such that signal in solution is low enough to permit signal differences at the array to be detected. For example, in one embodiment, the chamber is less than about 1 mm deep above the array; desirably the chamber is less than about 500 µm in depth. Typically, the chamber is less than about 400 µm, less than about 300 µm, less than about 200 µm, or less than about 150 µm in depth above the array. In one example provided herein, the chamber is about 142 µm in depth.

A "high-efficiency nucleic acid array" is an array of capture nucleic acids that efficiently hybridize to a probe or probe fragment under hybridization conditions. In typical embodiments, the array is formatted on an inner surface of a reaction/detection chamber. The array can be formed by any conventional array technology, from spotting to chemical or photochemical synthesis on the surface. High efficiency is achieved by controlling the length of the region of the capture probe that recognizes the probe or fragment (shorter probes hybridize more efficiently than long probes, down to a minimum hybridization length for the hybridization conditions), and by controlling the number of capture nucleic acids in each array region. Capture sites can be made more efficient/available for hybridization by including a linking sequence or structure between the capture site and the surface (thus formatting the capture sites at a selected distance from the surface, which can reduce surface effects on hybridization). For example, nucleic acid sequences or polyethylene glycol linkers (or both) can be used. The number of capture nucleic acids in each array region are distributed such that the number of sites available for hybridization for a given probe or fragment produced as a result of a typical amplification reaction is not rate limiting. As noted previously, this means that the number of sites available for binding labeled probe fragments produced during the amplification reaction is in excess, and preferably substantially in excess of the number of sites that would be saturated by the concentration of probe fragments in the reaction mixture after the amplification reaction.

A "labeled probe" is a molecule or compound that specifically hybridizes to a target nucleic acid under amplification conditions, and that comprises a moiety that is detectable, or that can be made detectable. Most typically, the labeled probe is a nucleic acid that comprises an optical label such as a fluorophore, dye, lumophore, quantum dot, or the like. The label can be directly detectable, or can be in a quenched state, e.g., where the probe comprises a quencher moiety. In many embodiments herein, the labeled probe is cleaved during target nucleic acid amplification to release a probe fragment comprising a detectable label. For example, the labeled probe can include a fluorophore and a quencher, e.g., where an amplification reaction results in cleavage of the probe to release the labeled probe fragment. Most typically, the probe will include a "flap" region. This flap region does not base-pair with the target during hybridization, and is cleaved from the rest of the probe by a nuclease (e.g., nuclease activity of a polymerase), thereby forming the probe fragment.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example Detection System

The detection system of this example allows for single chamber, multiplexed, real time PCR detection of a target nucleic acid. The system extends the multiplexing capability of real time PCR by moving from traditional spectral discrimination to array-based spatial discrimination to generate real time information specific to each target being amplified.

Traditionally, single well multiplexing is achieved by using PCR probes such as TAQMAN™ probes that are specific to each amplicon and that are labeled with fluorophores of different wavelengths. This approach limits single-reaction multiplexing capability to a maximum of about 5 targets, due to limits on dye emission spectra and the spectral window.

The approach described in this example uses a labeled PCR probe that acts as a surrogate for the amplicon to transfer information about the progression of amplification to a surface bound array during the process. Information about the kinetics of amplification is preserved, allowing for both detection and quantitative information to be obtained, based on a cycle number thresholding method.

During the extension step in the PCR cycle, the 5'-3' nuclease activity of Taq Polymerase cleaves the PCR probe to release a flap nucleic acid that can then preferentially hybridize to a capture probe on the array surface. Each flap and corresponding capture probe is unique to a potential target within the test panel.

Reaction Chamber Depth

Figure 13:
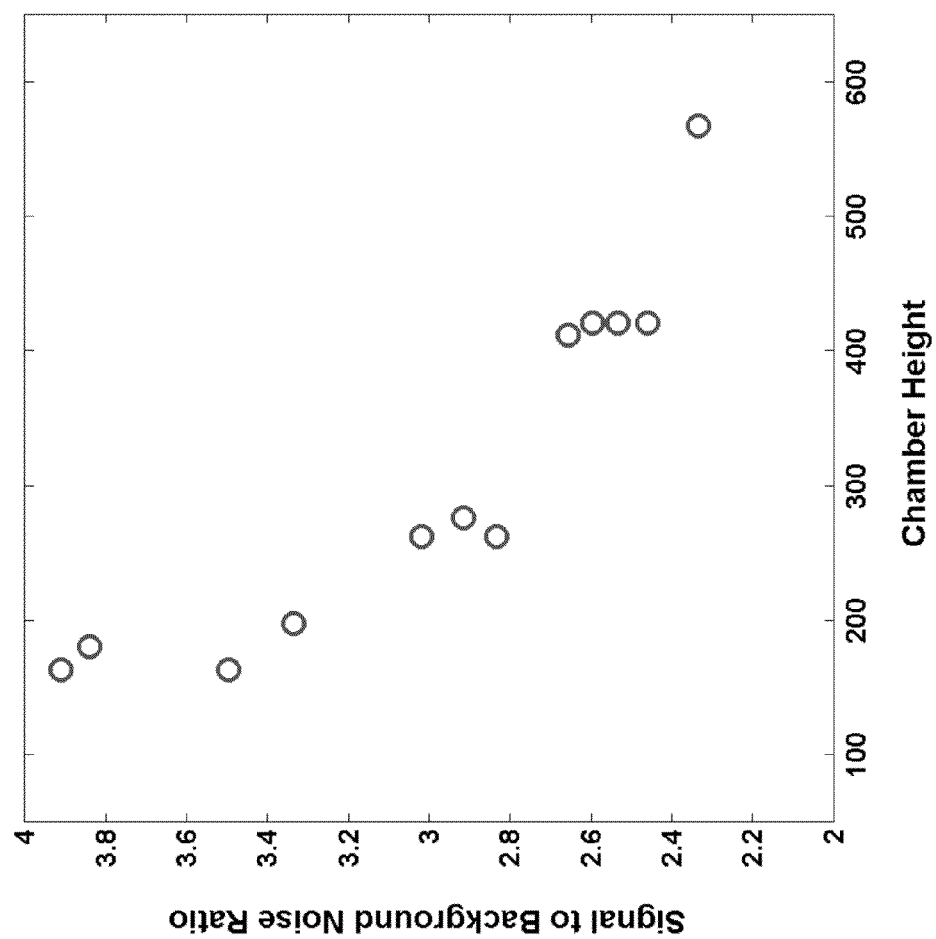
FIG. 13 is a plot showing the relation of reaction chamber thickness to the signal to background ratio.

An experiment was conducted to evaluate the relationship of chamber thickness to the Signal to Background Noise Ratio for a given array. Substrates were machined with chambers of varying depths and coated with functionalized polymer. Actual depths of the chambers were measured. The substrates were then spotted with the capture probes and assembled into enclosed reaction chamber using UV cured epoxy. A solution containing 45 nM of a synthetic mimic of the labeled probe fragment complementary to each capture probe on the array and 255 nM of the corresponding intact probe (to mimic 15% cleavage) was pipetted into each enclosed reaction chamber and the signal vs. background signal was measured after a 3 min hybridization at 30 C. Results for one of the assays is shown in FIG. 13. As can be seen, reduction in the thickness of the reaction chamber from 600 microns to below 200 microns showed a dramatic increase in the signal to background noise ratio, with optimal ratios below 300 microns and preferably below 200 microns thickness.

PCR Chamber and Array

The PCR chamber used in most of the experiments is shown in FIG. 2. As shown, the chamber consists of a bottom surface containing an array of capture oligos complimentary to the flap sequence of the PCR probes. The capture probes were synthesized by Integrated DNA Technologies Inc. (Coralville, Iowa) and have a 5' terminal amine group for covalent attachment to the substrate forming the bottom of the PCR chamber, along with a polyethylene glycol linker between the attachment chemistry and the oligo sequence. The length of the sequence is the same as the corresponding PCR probe flap. The bottom of the PCR chamber was formed from a commercially available slide. This slide came with a polymeric coating containing active NHS esters for subsequent attachment of the capture probes. Slides included both glass and plastic substrates coated with the polymeric coating. Both types of slides result in similar experimental data. The capture probes are spotted using a SPOTBOT™ (Arrayit Technologies (Sunnyvale, Calif.)) according to standard array protocols. The capture probe spots were typically 100 µm in diameter with a 200 µm center to center pitch between spots.

After spotting and washing of the capture probes, the PCR chamber was assembled using a pressure sensitive adhesive (PSA) and a polycarbonate top piece with inlet and outlet ports as shown in FIG. 2. The chamber had a final depth/thickness (or height) of 142 µM and a diameter of 15 mm. The chamber holds a volume of approximately 45 uL of PCR reagents.

Thermocycler and Optics Breadboard.

The thermocycling and optical detection system included an epifluorescent, single-channel detection system that includes (1) an excitation light source (e.g., a mercury arc lamp or an LED), (2) interference optical filters that are used for the excitation light and for the emission light so that specific combination of fluorophores are detected, such as Cy3, Cy5 or others, and (3) a photo-detector, which is a CCD or CMOS camera.

The system also included thermocycling components such as a pair of thermoelectric modules, metal plates, heat sinks and powerful cooling fans that were used to rapidly thermocycle an enclosed consumable (e.g., the array and chamber described above) to desired temperatures and for desired times. The thermoelectric modules were controlled to specific temperatures for specific time periods by the use of a feedback enabled control system that used thermistors proximate to the consumable as the feedback to the control system.

System control was performed by a computer, which used a script file as input to generate the target temperatures and time periods as well as to specify when an image was to be taken by the photo-detector. The resulting images taken at different times during the thermal reaction were analyzed by the computer to generate intensity curves as a function of time and thereby derive the concentration of the target.

Single-channel fluorescent images were captured from the consumable at various times and temperatures during the progress of the thermal reactions. These fluorescent images were then analyzed to yield quantification of starting target nucleic acid concentrations. The fluorescent images were analyzed using a combination of mean gray intensity measurements, background correction and baseline adjustments. The background was measured locally for each spot in the array. The background was computed by measuring the fluorescent intensity of a concentric annulus of the solution surrounding the spot of interest. The signal from each spot was then corrected to account for the local background. The corrected signal from each spot was further normalized to account for variability in spotting as well as uneven illumination in the field of view. The average of the corrected intensity measurements obtained from the first few cycles, typically between cycle 5 and 15, were then used to adjust the baseline and normalize measurements from each spot.

Example 1

Three Step Amplification Reaction

The amplification reagent mix contained standard PCR reagents including two PCR amplification primers specific to each target being amplified, as well as a PCR probe specific to each target being amplified. The structure of typical probe is schematically shown in FIG. 1A. As shown, FIG. 1A probe region (A) represents a nucleic acid region of the probe that is complimentary to a target amplicon, designed using the same rules as is typical for a traditional real time PCR probe (e.g., as in a TAQMAN™ probe). Probe region (B) represents an orthogonal nucleic acid "flap" sequence that is complimentary to a corresponding capture probe (discussed below), but not the target nucleic acid. For purposes of illustration, this sequence is designed in one example to have a $T_m$ of between 40° and 46° C., although other probe designs can be substituted. In one example, the sequence length is about 13 or 14 bases. Probe region (C) represents a nucleic acid with a sequence that is complimentary to a portion of the sequence of nucleic acid region (B). This sequence is designed to facilitate the formation of a secondary structure of the full-length probe, e.g., with a $T_m$ of between 47 and 51 C. Quencher (D) represents an optional quencher molecule. Label (E) represents a fluorophore or other optically detectable label. The fluorophore Cy3 was used for the data presented below.

For the data in this example, PCR was performed with the following reagent formulation: 200 nM primers, 1×FAST START™ PCR buffer (available from Roche), 2-6 mM MgCl2, 0.5 mg/mL BSA, 0.2 units/uL FAST START Taq polymerase (Roche), and 150 nM of PCR Probe.

100 uL PCR reactions were prepared using the formulation described above. The PCR Probe sequence that was used in this example was:

(SEQ ID NO: 1)
<u>NNNNNNNNNNNNNNN</u>CCTGTTGCCAATTTCAGAGTGTTTTGCTTAAC<u>NNNN</u>

<u>NNNNN</u>GAT.

The 5' and 3' flaps are denoted in underline/double underline and the traditional TaqMan sequence is shown in bold. The double underlined sequences denote the homologous regions designed to form secondary structure. The predicted melting temperature of the secondary structure was 51° C., as determined by mFold (idtdna.com) using the PCR buffer conditions. The PCR probe was labeled with a 5' Cy3 fluorophore and a Black Hole Quencher 2 moiety on the 3' end.

The capture probe sequence attached to the bottom substrate of the PCR chamber was: NNN NNN NNN NNN N with a $T_m$ of 42° C. using the PCR buffer conditions.

DNA plasmids comprising a target sequence were added to each PCR reaction at a concentration of $10^6$, $10^4$, and $10^2$ copies/uL. The solution was then degassed by heating to 95° C. After degassing, polymerase was added and the reaction was loaded into the PCR chamber using a pipette. Left over solution was loaded onto an Applied Biosystems 7500 for parallel analysis.

The cycling conditions for the array based PCR were as follows:

| Temp | Time | Purpose |
| --- | --- | --- |
| 95° C. | 120 sec | Fast Start Enzyme activation |
| 95 C. | 15 sec | denaturation |
| 60 C. | 60 sec | polymerase extension |
| 30 C. | 120 sec | Flap hybridization and optical reading |

(denaturation and extension were performed for 5 cycles, and then denaturation/extension/flap hybridization and optical reading are repeated for 8 cycles).

The Cycling conditions for the ABI 7500 were as follows:

| Temp | Time | Purpose |
| --- | --- | --- |
| 95° C. | 120 sec | Fast Start Enzyme activation |
| 95° C. | 15 sec | denaturation |
| 60° C. | 60 sec | polymerase extension and optical reading |

Denaturation/extension and reading were performed for 40 cycles.

Figure 3:
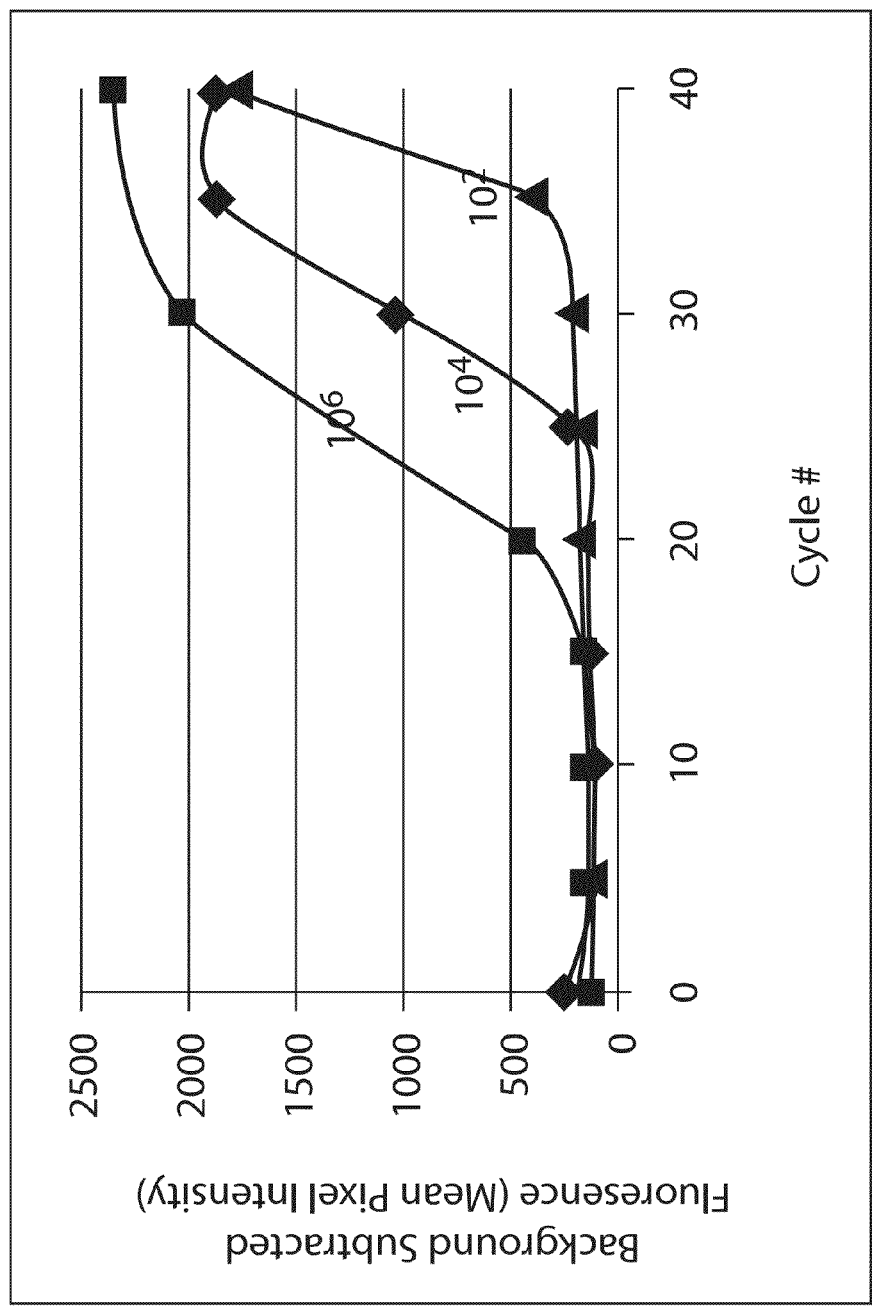
FIG. 3 is a graph showing array based real time PCR curves for copy number titration for a three step amplification reaction.
Figure 4:
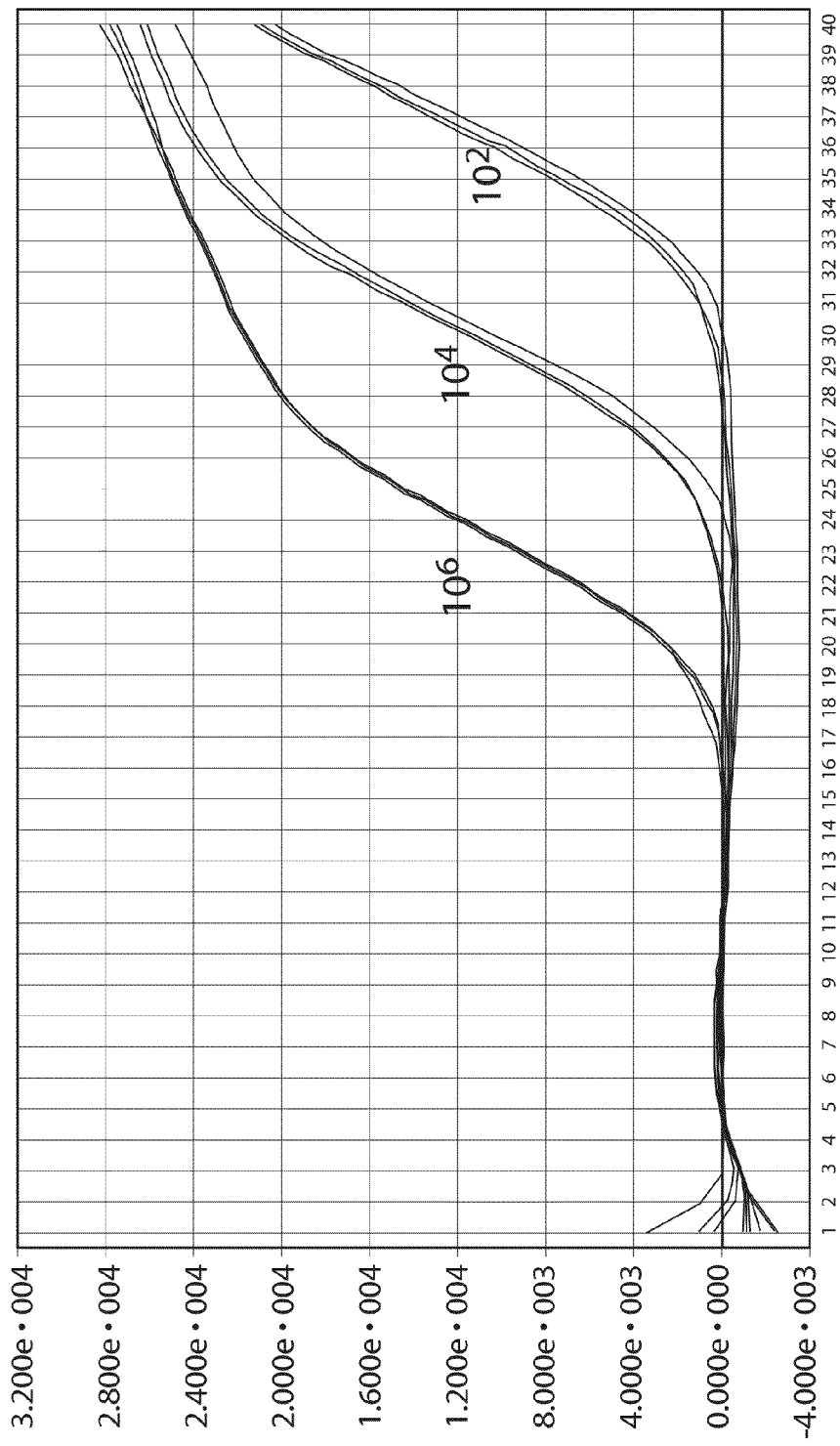
FIG. 4 is a graph showing solution based real time PCR curves generated from aliquots of solutions.

The results for the copy number titrations are shown in FIG. 3 for the array based PCR and FIG. 4 for the solution phase PCR. As can be seen from the figures, the results are comparable, giving similar behavior for the titrations.

Example 2

Two Step Amplification Reaction

Figure 1B:
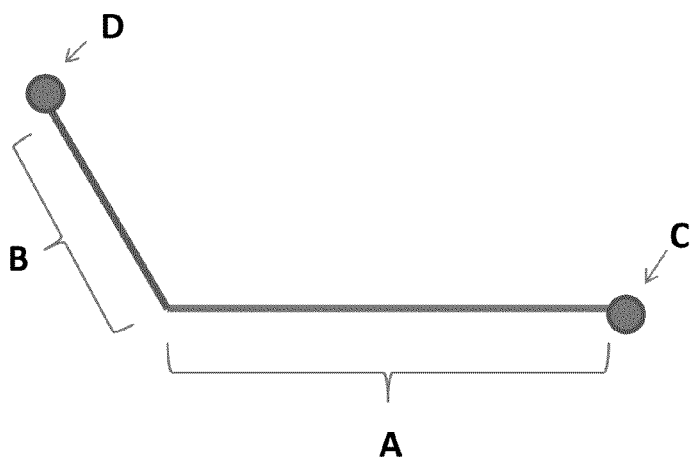

As with Example 1, above, the amplification reagent mix contained standard PCR reagents including two PCR primers (200 nM) complementary to each target being amplified as well as a PCR probe (300 nM) having a sequence complementary to each target being amplified. The structure of typical probe is shown in FIG. 1B. As shown, the labeled probe again includes a nucleic acid fragment (A) that is complimentary to a target amplicon designed using the same rules as is typical for a traditional real time PCR probe (i.e. TaqMan). Also included is orthogonal nucleic acid "flap" sequence (B) that is complimentary to a corresponding capture probe on the capture array. The probe also includes a fluorescent label (C) coupled to the flap portion B and a quencher moiety (D) coupled to the target specific portion (A).

For the two step amplification, the orthogonal flap (B) comprises a sequence that was designed to have a $T'_m$ with its complement on the capture array of 70° C. Typically the sequence length is 25 to 27 bases. As with Example 1, above, the overall probe is designed so that the most stable secondary structure has a $T_{in}$ no higher than 10° C. below the extension and measurement temperature in the buffer conditions used for PCR. The oligo was designed using the unafold software available from Integrated DNA Technologies, Inc. The following PCR probe sequence was used in this example:

(SEQ ID NO: 40)
<u>NNN NNN NNN NNN NNN NNN N/Cy3/NN NNN NNN</u> ATG GCC GTT AGC TTC AGT CAA TTC AAC AG/BHQ_2/

Where the double underlined sequence constitutes the orthogonal flap and the non-underlined sequence is homologous to the amplicon. The most stable secondary structure of the probe has a melting temperature of 45° C. The $T_m$ of the orthogonal flap is 71° C. The PCR probe was labeled with an internal Cy3 fluorophore C (available from GE Healthcare Biosciences, Piscataway, N.J.) and a Black Hole Quencher 2 moiety D (available from Biosearch, Inc., Novato, Calif.) on the 3' end.

A capture probe was spotted that was homologous to the flap portion of the PCR Probe. PCR was performed, as above, except with the following cycling conditions:

| Temp | Time | Purpose |
| --- | --- | --- |
| 95° C. | 60 sec | Fast Start Enzyme activation |
| 95 C. | 15 sec | denaturation |
| 55 C. | 60 sec | polymerase extension, flap hybridization and optical reading |

Figure 12:
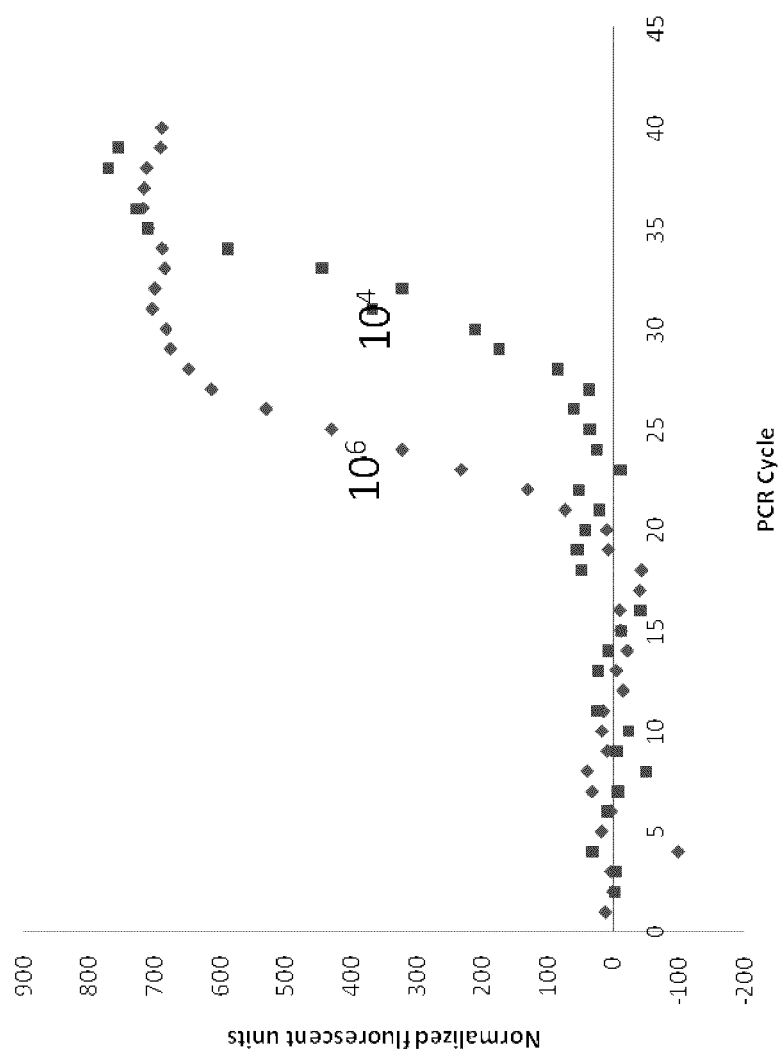
FIG. 12 is a graph showing array based real time PCR curves for copy number titration for a two step amplification reaction.

Forty cycles were carried out and with the fluorescent signal being measured at the end of each extension step. FIG. 12 shows the copy number titrations for the array based PCR for two targets where the first was present at the outset at $10^4$ copies of target DNA plasmid while the second was present at $10^6$ copies.

Example 3

Array Based PCR Curve Using an Unquenched PCR Probe

The same protocol was used as in Example 1 with the following exceptions. The PCR probe sequence used is as follows:

```
                                                     (SEQ ID NO: 3)
NNNNNNNNNNNNNNTCGCTGAACAAGCAACCGTTACCCNNNNNNNN
```

Figure 5:
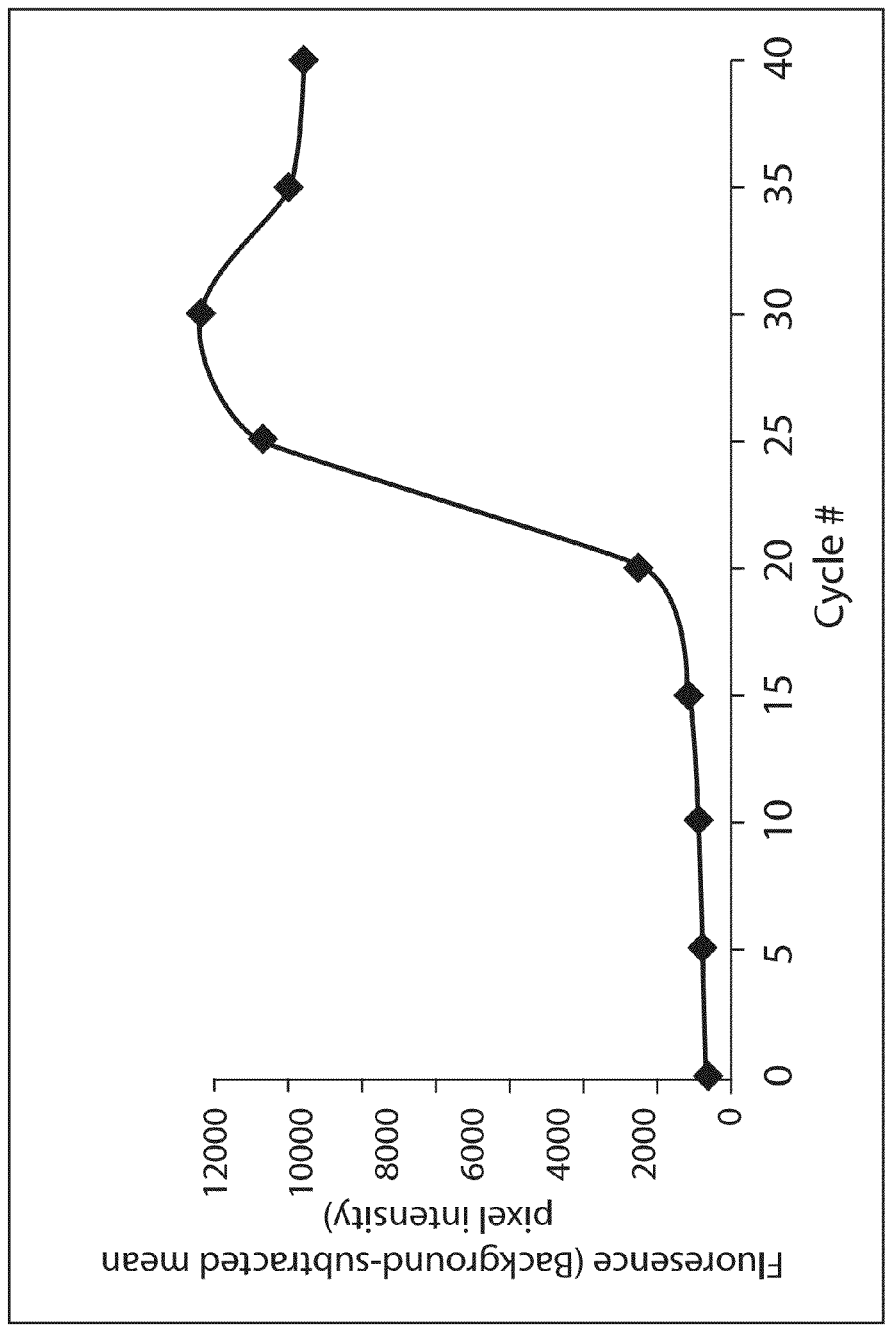
FIG. 5 is a graph showing an array based real time PCR curve generated with an unquenched probe.

This sequence was labeled with a 5' Cy3 fluorophore, but did not include a 3' quencher. $10^6$ copies of target were added and the PCR was run. The real time data is shown in FIG. 5.

Example 4

Multiplexed Array Based Amplification

This experiment establishes the ability to interrogate for and amplify multiple targets within the same PCR chamber. PCR conditions are the same as shown in Example 1 except for the following exceptions: first, 5 sets of primers and 5 separate PCR probes are added to the PCR reaction specific to each target to be interrogated. Second, 5 unique capture probes are deposited onto the bottom substrate of the PCR chamber corresponding to the 5' flap sequence of each of the 5 PCR probes. Third, after the 10th PCR cycle the temperature was dropped to the surface hybridization temperature of 30° C. every 2 cycles instead of every 5 cycles as in Example 1. This allows for a higher frequency of optical interrogation during the PCR amplification.

The PCR probe and capture probe sequences are shown below:

PCR Probes:

```
Flu A:
                                                     (SEQ ID NO: 4)
NNNNNNNNNNNNNNCCCCAT GGAATGTTAT

CTCCCTTTTAAGCTTCTNNNNNNNN  (T_m of 50.3°)

A/H1:
                                                     (SEQ ID NO: 5)
NNNNNNNNNNNNNACCTTGGC GCTATTAGAT TTCCATTTGC

CNNNNNNNN  (T_m of 51.2°)

A/H3:
                                                     (SEQ ID NO: 6)
NNNNNNNNNNNNNNNCCTGTT GCCAATTT CAGAGTGTT

TTGCTTAACNNNNNNNNNNNN  (T_m of 51°)

FluB:
                                                     (SEQ ID NO: 7)
NNNNNNNNNNNNNNNTCAAAGC CAATTCGAG CAGCTGAAAC

TNNNNNNNN  (T_m of 51°)

phiMS2:
                                                     (SEQ ID NO: 8)
NNNNNNNNNNNNNNTCGCTGAA CAAGCAACC GTTACCCNNNNNNNNNNNNN  (T_m of 52°)
```

Capture Probes

```
      FluA:
      NNN NNN NNN NNN N  (T_m of 46°)

A/H1:
      NNN NNN NNN NNN N  (T_m of 45°)

A/H3:
      NNN NNN NNN NNN N  (T_m of 42°)

FluB:
      NNN NNN NNN NNN N  (T_m of 46°)

phiMS2:
      NNN NNN NNN NNN N  (T_m of 43°)
```

Figure 6:
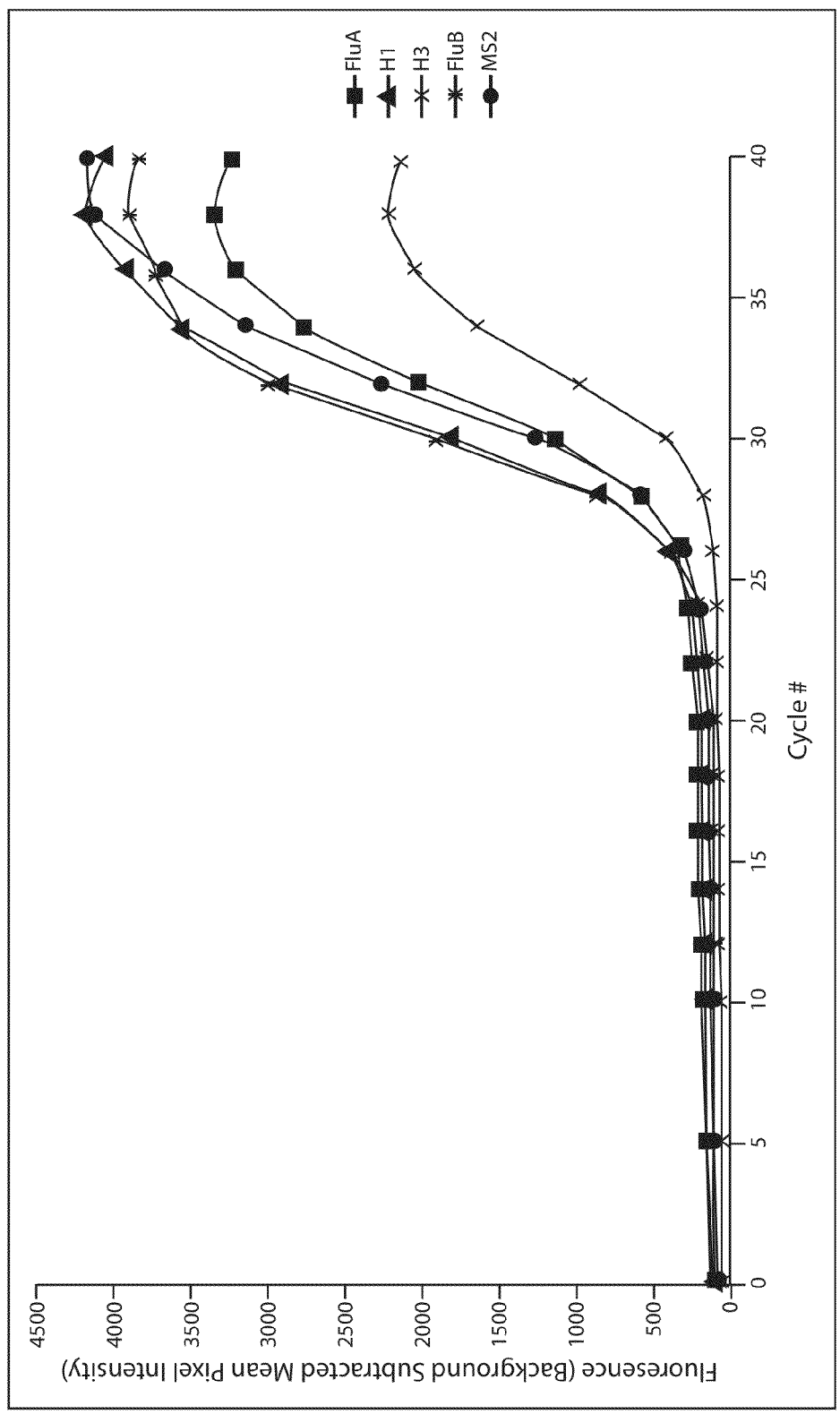
FIG. 6 is a graph showing real time PCR curves for a multiplexed amplification.

5 targets plasmids encompassing the sequences specific to the primers and PCR probes above were added to a 100 uL PCR reaction and the solution was prepped and loaded as described in above. The resulting real time array based PCR data is shown in FIG. 6.

Example 5

High Level Multiplexing

This example demonstrates single chamber multiplexing for detection of multiple targets that can be any of the ten potential targets included in the panel of this example. This level of multiplexing—a panel of more than five potential targets—cannot be achieved in traditional solution phase PCR.

The experimental materials and procedures were the same as that above except for the following: first, 10 Primer sets and PCR probes were incorporated into PCR reaction in the same concentrations as above. The sequences of the PCR probes and capture probes are given below:

PCR Probes:

```
FluA:
                                                     (SEQ ID NO: 9)
NNNNNNNNNN NNCCCCATGG AATGTTATCT CCCTTTTAAG

CTTCTNNNNNNNN  (T_m of 50.3°)

A/H1:
                                                     (SEQ ID NO: 10)
NNNNNNNNNNNNNNNACCTTGGCGCT ATTAGATTTC

CATTTGCCNNNNNNNN  (T_m of 51.2°)

A/H3:
                                                     (SEQ ID NO: 11)
NNNNNNNNNNNNNNCCTGTTGCCA ATTTCAGAG TGTTTTGCT

TAACNNNNNNNNNNN  (T_m of 51°)

FluB-v2:
                                                     (SEQ ID NO: 12)
NNNNNNNNNNNNNNNTCAAAGCC AATTCGAGCA GCTGAAAC

TNNNNNNNN  (T_m of 51°)

phiMS2:
                                                     (SEQ ID NO: 13)
NNNNNNNNN NNNNTCGCTG AACAAGCAA CCGTTACCC NNNNNNNN (T_m of 52°)

MPV:
                                                     (SEQ ID NO: 14)
NNNNNNNNNNNNNNATGG CCGTTAGCTT CAGTCAATTC

AACAGNNNNNNN  (T_m of 48.4°)

PIV1:
                                                     (SEQ ID NO: 15)
NNNNNNNNNNNNNNTTGGAATT GTCTCGACA ACAATCTTTG

GCCTNNNNNNNN  (T_m of 50.4°)
```

-continued

PIV2:
(SEQ ID NO: 16)
NNNNNNNNNNNNNCCATTT ACCTAAGTGA TGGAATCAAT

CGCAAAAGNNNNNNNN ($T_m$ of 48.8°)

PIV3:
(SEQ ID NO: 17)
NNNNNNNNNNNNNNNACATAA GCTTTGATC AACCCTATG

CTGCACNNNNNNNNN ($T_m$ of 49.9°)

RSV:
(SEQ ID NO: 18)
NNNNNNNNNN NNNTTCGAAGGCTC CACATACACAG CTGCTGNNNNN

NNNN ($T_m$ of 49.9°)

RSV-v2:
(SEQ ID NO: 19)
NNNNNNNNNNNNNNTCGAAGGC TCCACATACA CAGCTGCTGNNNNNNNNN ($T_m$ of 51°)

OPC1:
(SEQ ID NO: 20)
NNNNNNNNNNNNNNNTTCGGCAT TTCCTGGATTGAGT

CGGTACTANNNNNNNN ($T_m$ of 48.7°)

Capture Probes

| | Capture Probe $T_m$ | |
|---|---|---|
| FluA | NNN NNN NNN NNN N | ($T_m$ of 46°) |
| A/H1 | NNN NNN NNN NNN N | ($T_m$ of 45°) |
| A/H3 | NNN NNN NNN NNN N | ($T_m$ of 42°) |
| FluB-v2 | NNN NNN NNN NNN N | ($T_m$ of 46°) |
| phiMS2 | NNN NNN NNN NNN N | ($T_m$ of 43°) |
| MPV | NNN NNN NNN NNN N | |
| PIV1 | NNN NNN NNN NNN N | |
| PIV2 | NNN NNN NNN NNN N | |
| PIV3 | NNN NNN NNN NNN N | |
| RSV | NNN NNN NNN NNN N | |
| RSV-v2 | NNN NNN NNN NNN N | |
| OPC1 | NNN NNN NNN NNN N | |

Figure 7:
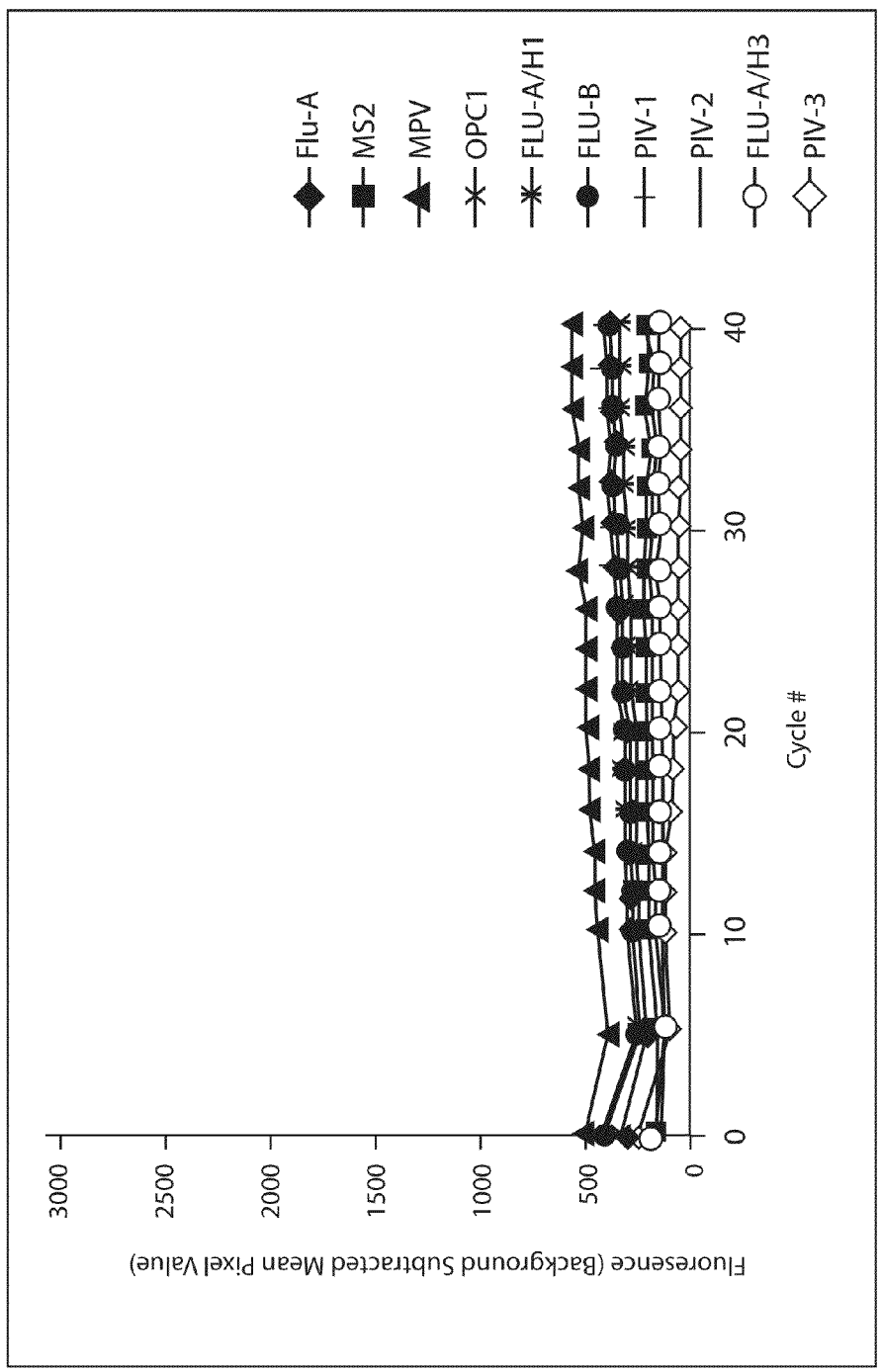
FIG. 7 is a graph showing array-based real time PCR curves for a 10-plex reaction with no target added.
Figure 8:
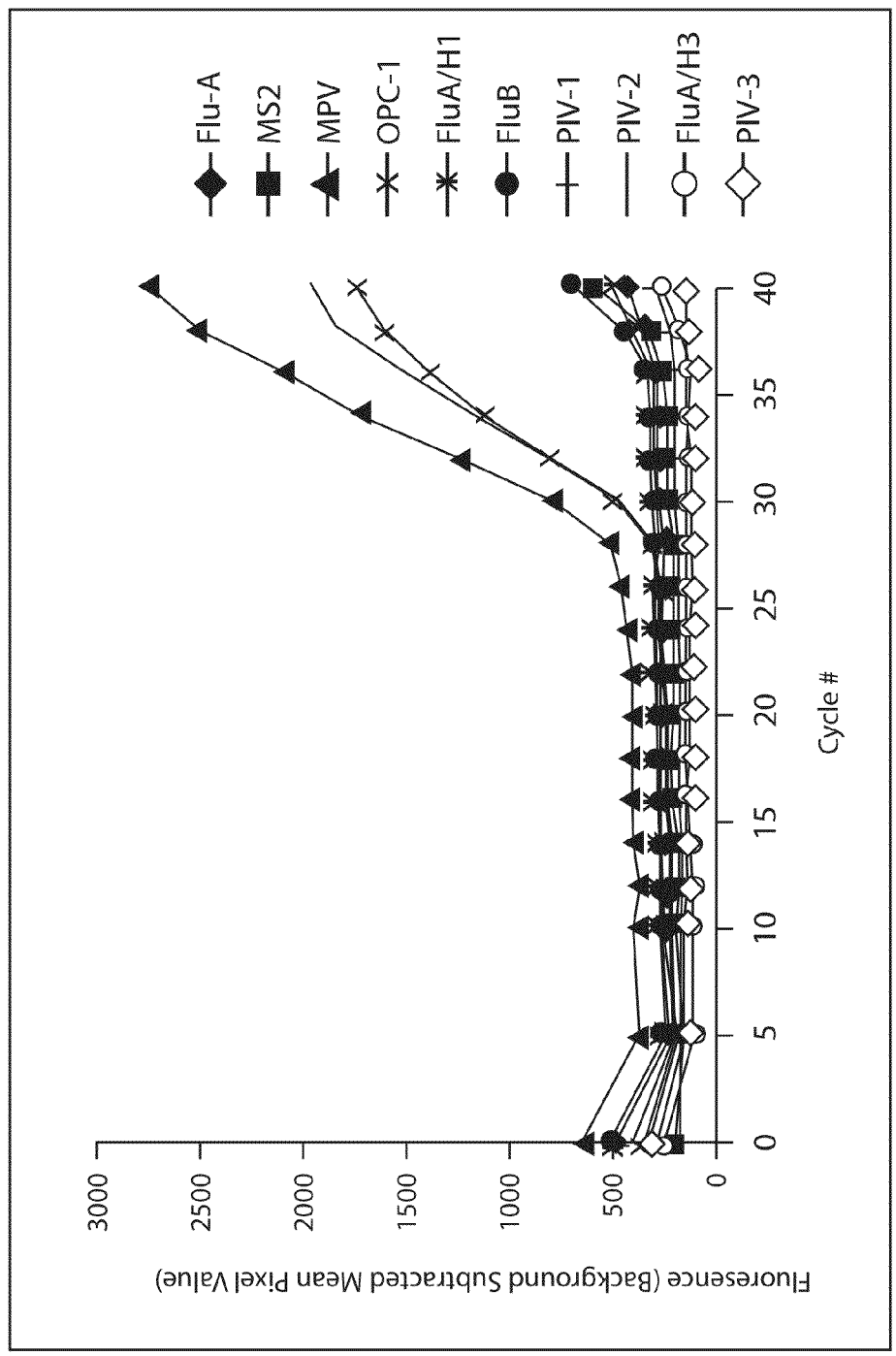
FIG. 8 is a graph showing array-based real time PCR curves with a 10-plex panel and 3 targets present at $10^4$ copies each.

FIG. 7 shows the resulting real time array-based PCR curves when no target was added to the PCR reactions (No Template Control). As can be seen from the figure, no signal was obtained from a solution containing all PCR components except target. FIG. 8 shows the same experiment with 3 plasmid targets (MPV, OPC-1, PIV2) added at 10,000 copies/uL.

Example 6

Demonstration of Fast Hybridization Kinetics

A PCR chamber was constructed as described above. The following amine, pegylated capture probe sequence was deposited on the bottom substrate: NNN NNN NNN NNN N.

A solution containing the PCR buffer described above was prepared containing the following oligo sequence (100 nM) which mimics the 5' flap portion of the PCR probe, labeled with a Cy3 fluorophore on the 5' end and complimentary to the capture probe: NNN NNN NNN NNN N.

Figure 9:
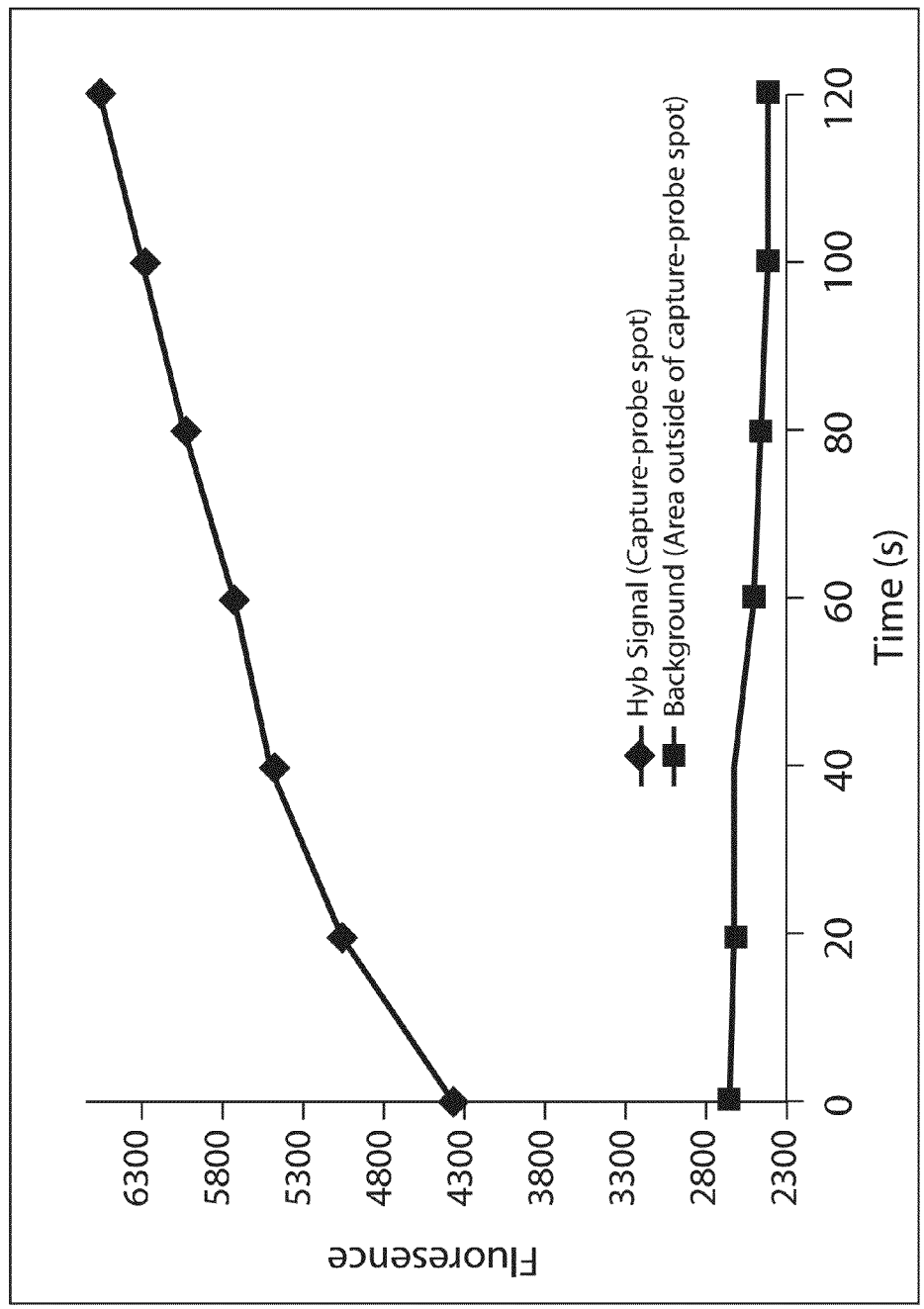
FIG. 9 is a graph showing real-time kinetics of hybridization of a 5' flap mimic.

The solution was loaded into the PCR chamber and the chamber was heated to 60° C. (15 degrees above the $T_m$ of the duplex) and then cooled back down to 30° C. This mimics the conditions during the hybridization step of the PCR protocol. An optical reading was taken every 20 sec for 2 min. The resulting data is shown in FIG. 9.

One interesting aspect of the data shows that there is already significant hybridization occurring at the instant that the internal temperature reaches 30° C.

Example 7

Dark Assay Configuration

The three step amplification assay described in Example 1, above, was repeated using a flap portion of the probe that included an Iowa Black RQ quencher group available from Integrated DNA Technologies, coupled to its 5' end, and without any other labeling or quenching groups attached to the probe. The capture probes deposited upon the array surface carried a Cy3 fluorophore coupled to the 3' terminus.

All primer and probe sequences were ordered from IDT and received lyophilized. They were then resuspended in water to stock concentrations (100 uM to 200 uM) and used to prepare primer/probe stock solutions for PCR reactions. H03 NVS PCR buffer, was combined with primers and probes to make a PCR master mix.

Functionalized surfaces (COP substrates coated with functionalized polymer) were spotted using traditional microarray spotting techniques via an Array-It spotbot 2. Spotted slides were incubated at 75% humidity for 8-15 hours and were then rinsed with DI water and dried with argon. Labeled capture probes were spotted in concentrations ranging from 100 nM to 50 uM in 50 mM pH 8.5 spotting buffer, producing a range of signal intensities.

As with the examples above, the chip based reaction chambers were built on top of functionalized, arrayed surfaces using double sided pressure sensitive adhesive gaskets, polycarbonate lids and optically clear seals. Total volume of the reaction chamber is approximately 30 uL with a height of 150 um.

Target sequences of a known concentration are added to PCR master mix and the resulting solution is loaded in the reaction vessel. The vessel was sealed and loaded on a the above-described thermocycling instrument. The target sequences were obtained from plasmid stocks or the resulting amplicons from previous reactions involving those amplicon stocks. All target molecules were quantitated using UV-Vis spectrometry on a NanoDrop instrument.

Figure 15:
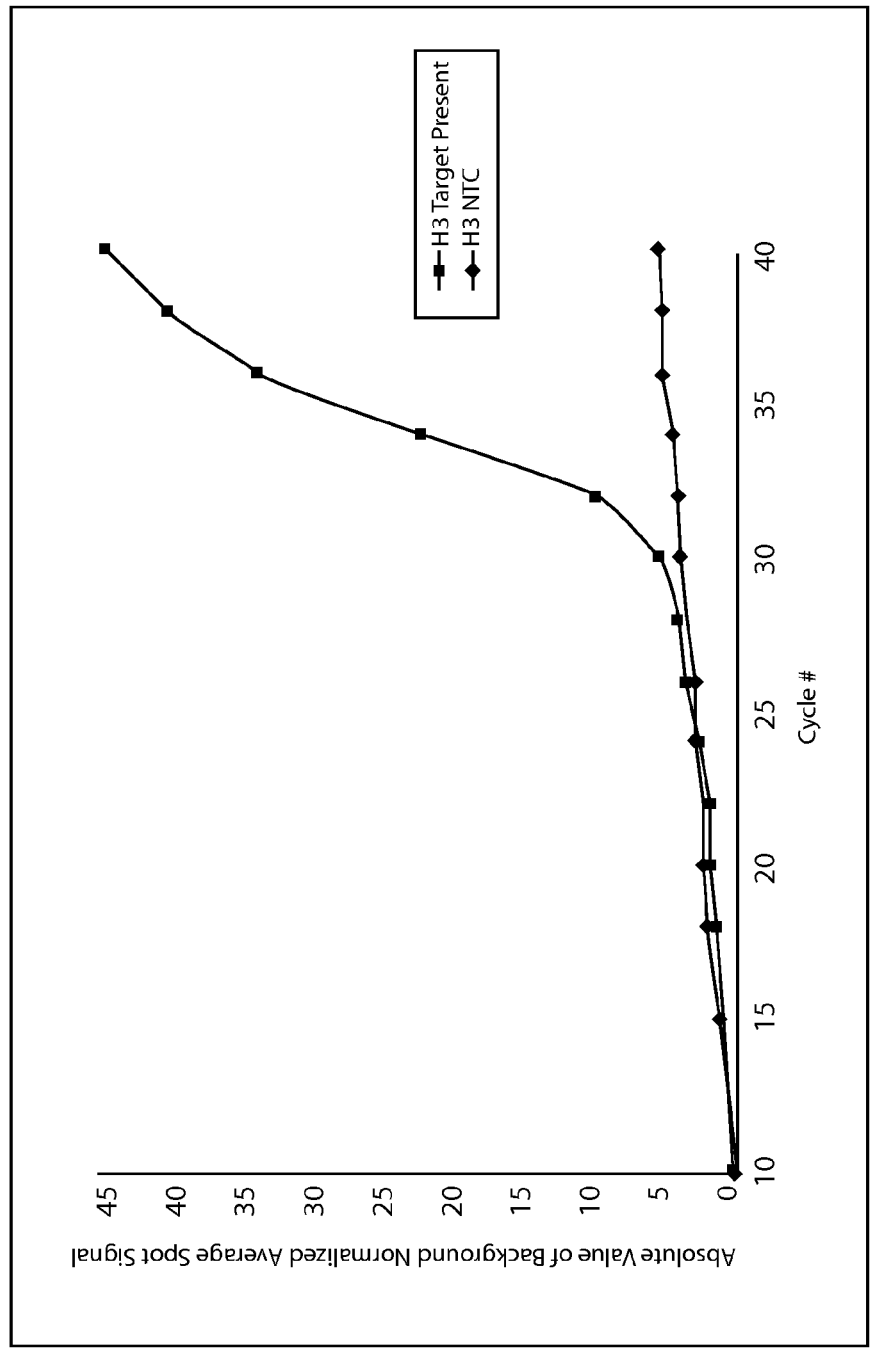
FIG. 15 is a plot of real time PCR using quencher bearing probes, with decreasing fluorescent signal over the reaction's progress.

Thermocycling conditions included a hot start step at 95 C for 85 s, followed by 40 cycles of melt (95 C) and extension (55 C) of 5 s and 20 s respectively. At cycles 10, 15, 18, and every 2 cycles thereafter, an additional step is added to the cycle for data collection. The temperature is brought to 30 C following extension, and held for 30 s. Images of the surface are collected at the end of these hybridization steps. Average pixel intensity in the spots for each assay is calculated and plotted vs cycle number to generate real-time PCR curves. The solution and surface probe designs are as depicted in assay format 3. For duplex PCR reactions: 600 nM primers and 300 nM probes for the H3 and OPC1 assays are added. FIG. 15 shows a plot of the progress of the real time PCR reaction based upon the increasing hybridization of flap portions and their associated quenchers to the Cy3 labeled capture probes. The fluorescent signal is plotted as an absolute value of the negative signal, showing the decrease in signal as the reaction progresses.

The approaches outlined herein have multiple advantages not found in previous approaches. The systems of the invention allow for single chamber, highly multiplexed, quantitative PCR by efficiently transferring information from solution phase PCR to a surface confined array in real time during the amplification process. This allows for a much higher level of multiplexing while preserving the efficiency and leveraging the immense body of knowledge accumulated for solution phase real time PCR. In order to achieve this, multiple novel aspects of the system had to be developed.

For example, one feature of the invention is the use of an amplicon surrogate to bridge the solution phase and the solid phase. Previous teachings aimed towards the goal of array based real time PCR have generally relied upon hybridization of the amplicon itself to the solid phase array. This presents multiple issues that complicate the system, hinder the efficiency, and require more expensive components to elucidate the required information. In a multiplexed PCR environment, it is very hard to design amplicons of similar lengths and hybridization efficiencies. The use of a PCR probe with a cleavable 5' flap homogenizes the species that transfers the information from each amplicon to the surface by employing a very short sequence that is ideal for hybridization kinetics. This approach also makes the capture probe sequences on the array independent of the sequence of the amplicon to be detected. This allows for selection of the most advantageous capture sequences and the possibility of a universal array that can be used for many different target panels, simplifying the design and manufacturing approach.

As disclosed here, the PCR probe also leverages the design rules that have already been developed for probe based solution phase real time PCR. The use of a very short sequence for hybridization (e.g., 13-14 bases) makes the hybridization very efficient, allowing for high signal on the array in the low salt environment of standard PCR buffers. Thus the system can work very well in a single chamber where surface hybridization has to be coupled with optimal solution phase PCR.

Another feature of the invention is the discrimination of surface hybridized signal from solution phase background fluorescence. This aspect of the invention is important in extracting relevant information from the array. Previous teachings employ complicated or expensive optical approaches to overcome this problem, such the use of total internal reflectance or confocal microscopy to isolate the surface signal from the solution background. By contrast, this invention provides the use of simple standard optical equipment that require no optical "tricks" to achieve discrimination. The ability to discriminate the signal arises from multiple sources. The surface chemistry that is used in the array provides a very high capture probe density and thus hybridized target density. It has been shown that the surface can approach 100% capture efficiency of target nucleic acid. This high capture density and efficiency serves to concentrate the surface signal, aiding in surface/solution phase discrimination. The use of a short target nucleic acid serves to dramatically enhance this effect.

Another aspect of the invention that aids in the signal discrimination is the use of a very thin PCR chamber. The background signal from the solution is linearly related to the height of solution above the array. The use of a thin chamber takes advantage of this effect.

Another aspect of the invention is the use of fast hybridization kinetics to allow for real time transfer of the solution phase information to the surface array. The system described in these examples demonstrates extremely fast solid phase hybridization. This phenomenon facilitates the technology and can be attributed to multiple aspects of the invention, including the short 5' flap target, the optimal solid phase surface chemistry, the thin consumable and the temperature gradient produced during the thermocycling temperature program.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.C-CCC

What is claimed is:

1. A method of detecting a target nucleic acid sequence in a sample, comprising:

performing an amplification reaction on the sample with a polymerase enzyme that possesses nuclease activity, in the presence of a reagent comprising first probes that comprise a first portion complementary to the target nucleic acid sequence and a second portion not complementary to the first target nucleic acid sequence, the second portion comprising a first quencher moiety coupled to the second portion at a first position, such that the second portion is cleaved from the first portion as a first probe fragment, when the target nucleic acid sequence is amplified;

hybridizing the first probe fragment to capture probes immobilized upon a substrate, wherein the capture probes comprise a fluorophore that is at least partially quenched by the first quencher moiety, the fluorophore coupled to a second position on the capture probes such that upon hybridization of the probe fragments to the capture probes, the fluorophore is at least partially quenched by the quencher; and detecting the presence of the target sequence based upon the quenching of the fluorophore on the capture probes.

2. The method of claim 1, wherein:

the amplification reagent comprises a plurality of different probes each different probe having a different first portions complementary to a different target nucleic acid sequences, and each different probe having a different second portions not complementary to a target nucleic acid sequences, the second portions of each different probe comprising a quencher moiety coupled to the first position, the second portion being cleaved as a probe fragments upon amplification of the plurality of target nucleic acid sequences; and wherein the substrate comprises a plurality of different capture probe regions arrayed on the substrate, each capture probe region comprising capture probes complementary to a different second portion of the plurality of different probes, and each capture probe comprising a fluorophore quenched by the quencher moiety.

3. The method of claim 1, wherein the first position comprises the 5' end of the probe fragment, and the second position comprises the 3' end of the capture probe.

4. The method of claim 2, wherein each capture probe region comprises a non-rate limiting number of capture nucleic acids that hybridize to the probe fragment.

5. The method of claim 1, wherein the first probe fragment that hybridizes to the capture probes is less than about 30 nucleotides in length.

6. The method of claim 1, wherein the first probe fragment that hybridizes to the capture probes is less than about 20 nucleotides in length.

7. The method of claim 1, wherein the first probe fragment that hybridizes to the capture probes is less than about 15 nucleotides or less in length.

8. The method of claim 1, wherein the target nucleic acid is amplified for at least 5 amplification cycles prior to said detecting.

9. The method of claim 1, wherein the target nucleic acid is amplified in a plurality of amplification cycles prior to said detecting, wherein the target nucleic acid portion is additionally amplified after said detecting, in the presence of additional copies of the probe, with resulting released first probe fragments being subsequently hybridized to the array and detected, wherein detected signal intensity is correlated to a quantity of the target nucleic acid present in the sample.

10. The method of claim 1, wherein a temperature of the hybridizing step is less than a temperature of the amplification reaction.

11. The method of claim 1, comprising detecting local background for one or more regions of the array, and normalizing signal intensity measurements by correcting for said background.

12. The method of claim 2, wherein the sample comprises a plurality of target nucleic acids.

13. The method of claim 2, wherein the plurality of different capture probes are spatially separated on the substrate.

14. The method of claim 2, wherein there are between about 5 and about 100 different capture probes, and between about 5 and about 100 corresponding probes in the amplification reaction, wherein up to 5 to 100 different signals can be detected based upon positioning of the signals in the array.

15. The method of claim 2, wherein the capture probes are arrayed on the substrate at a density of about between about 350 fmoles/cm$^2$ and about 5,000 fmoles/cm$^2$ or greater.

16. The method of claim 2, wherein the capture probes are arrayed on the substrate at a density greater than 2000 firioles/cm$^2$.

17. The method of claim 2, wherein the plurality of different capture probes comprise the same fluorophore, and the plurality of different probe fragments comprise the same quencher moiety.

18. The method of claim 1, wherein the amplifying step and the step of hybridizing the first probe fragment to the substrate are carried out at the same temperature.

* * * * *

UNITED STATES PATENT AND TRADEMARK OFFICE
CERTIFICATE OF CORRECTION

PATENT NO. : 8,703,653 B2
APPLICATION NO. : 13/587883
DATED : April 22, 2014
INVENTOR(S) : Kris Scaboo et al.

It is certified that error appears in the above-identified patent and that said Letters Patent is hereby corrected as shown below:

In The Claims

Column 46

Line 57, delete "tions" and insert --tion--

Line 58, delete "sequences" and insert --sequence--

Line 59, delete "portions" and insert --portion--

Line 60, delete "sequences" and insert --sequence--

Line 60, delete "portions" and insert --portion--

Line 63, delete "fragments" and insert --fragment--

Signed and Sealed this
Ninth Day of August, 2016

Michelle K. Lee
*Director of the United States Patent and Trademark Office*